(12) United States Patent
Dickman et al.

(10) Patent No.: US 10,053,407 B2
(45) Date of Patent: Aug. 21, 2018

(54) CRYSTALLINE CANNABIDIVARIN

(71) Applicants: Daniel Dickman, San Ramon, CA (US); Emerich Eisenreich, Claremont, CA (US); Daniel Levin, La Canada, CA (US); Mackenzie Marrs, Pasadena, CA (US)

(72) Inventors: Daniel Dickman, San Ramon, CA (US); Emerich Eisenreich, Claremont, CA (US); Daniel Levin, La Canada, CA (US); Mackenzie Marrs, Pasadena, CA (US)

(73) Assignee: S&B Pharma, Inc., Azusa, CA (US)

( * ) Notice: Subject to any disclaimer, the term of this patent is extended or adjusted under 35 U.S.C. 154(b) by 0 days.

(21) Appl. No.: 15/609,159

(22) Filed: May 31, 2017

(65) Prior Publication Data

US 2017/0349517 A1 Dec. 7, 2017

Related U.S. Application Data

(60) Provisional application No. 62/344,005, filed on Jun. 1, 2016.

(51) Int. Cl.
*A61K 31/05* (2006.01)
*C07C 39/23* (2006.01)
*C07C 37/68* (2006.01)

(52) U.S. Cl.
CPC .............. *C07C 39/23* (2013.01); *C07C 37/68* (2013.01); *C07B 2200/13* (2013.01); *C07C 2601/16* (2017.05)

(58) Field of Classification Search
CPC ....................................... A61K 31/05
USPC ........................................... 514/733
See application file for complete search history.

(56) References Cited

U.S. PATENT DOCUMENTS 9,125,859 B2 9/2015 Whalley et al.
2015/0057342 A1 2/2015 Koren et al.
2016/0374958 A1* 12/2016 Anastassov ............ A61K 31/05
514/734

FOREIGN PATENT DOCUMENTS

EP 3061450 A1 † 8/2016
WO WO2013038157 A1 3/2013
WO 2016135308 A1 † 9/2016

* cited by examiner
† cited by third party

*Primary Examiner* — Raymond J Henley, III
(74) *Attorney, Agent, or Firm* — Sonapat LLC

(57) ABSTRACT

Solid cannabidivarin, crystalline cannabidivarin, (R,R)-(−)-crystalline cannabidivarin, (S,S)-(+)-crystalline cannabidivarin and substantially pure forms thereof are disclosed herein. Further disclosed are methods of making such cannabidivarin, compositions and formulations comprising such cannabidivarin, and methods of treating disease with such cannabidivarin.

23 Claims, 19 Drawing Sheets

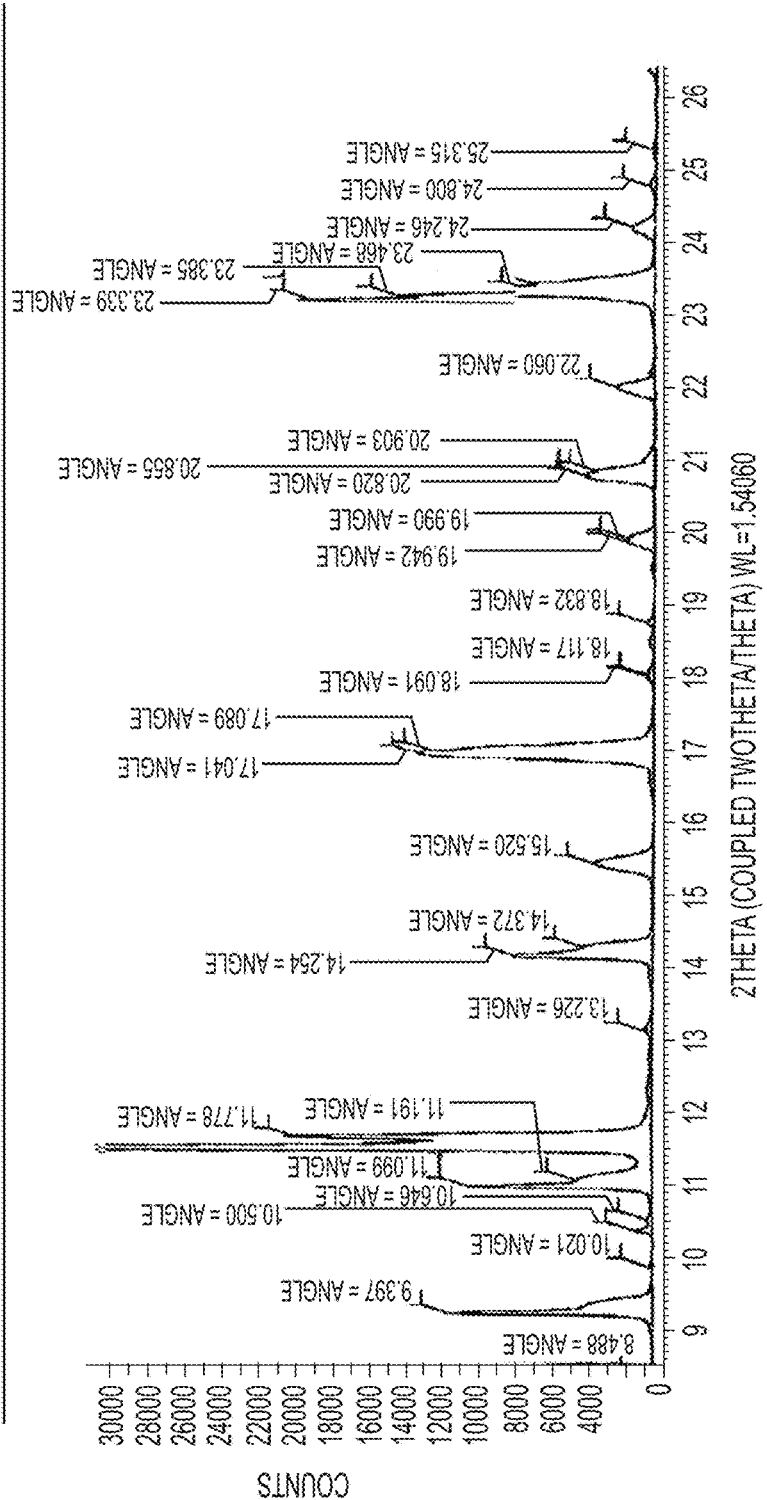

FIG. 5 DIFFERENTIAL SCANNING CALORIMETRY THERMOGRAM OF (R,R)-(−)-CRYSTALLINE CANNABIDIVARIN PREPARED WITH SEEDING

CRYSTALLINE CANNABIDIVARIN

This application claims benefit of U.S. Provisional Application No. 62/344,005, filed on Jun. 1, 2016, the entire contents of which are specifically incorporated by reference herein.

Cannabidivarin is a cannabinoid found in *Cannabis* and has been suggested as an agent for the treatment of epilepsy as set forth in U.S. Pat. No. 9,125,859, the contents of which are incorporated herein by reference. It has also been shown to have activity in cancer as shown in WO2013/038157, the contents of which are also incorporated herein by reference. Cannabidivarin is currently undergoing clinical trials for the treatment of epilepsy and other conditions. When isolated, cannabidivarin has been utilized as a non-crystalline plant extract or it has been formulated as a component of an oily plant extract (US 2015/0057342 A1). To date, no synthetic preparation of either solid cannabidivarin or a crystalline form of cannabidivarin has been reported.

SUMMARY OF THE INVENTION

In an aspect of the invention, solid cannabidivarin is provided.

In another aspect of the invention, synthetically-prepared solid cannabidivarin is provided.

In a further aspect of the invention, synthetically-prepared solid (R,R)-(−)-cannabidivarin is provided.

In still a further aspect of the invention, synthetically-prepared solid (S,S)-(+)-cannabidivarin is provided.

In one other aspect of the invention, crystalline cannabidivarin is provided.

In a further aspect of the invention, (R,R)-(−)-crystalline cannabidivarin is provided.

In yet another aspect of the invention, (S,S)-(+)-crystalline cannabidivarin is provided.

In a further aspect of the invention, a pharmaceutical formulation comprising solid cannabidivarin and one or more pharmaceutically acceptable excipients is provided.

In yet an additional aspect of the invention, a method for treating cancer or epilepsy comprising administering to a patient a pharmaceutically acceptable amount of solid cannabidivarin is provided.

In an additional aspect of the invention, a pharmaceutical formulation comprising cannabidivarin and one or more pharmaceutically acceptable excipients is provided wherein the cannabidivarin used to prepare the pharmaceutical formulation is crystalline.

In a further aspect of the invention, a method for treating cancer or epilepsy comprising administering to a patient a pharmaceutically acceptable amount of cannabidivarin in a pharmaceutical formulation is provided wherein the cannabidivarin used to prepare the pharmaceutical formulation is crystalline.

Amorphous cannabidivarin is another aspect of the invention.

In a still further aspect of the invention, a process for making crystalline cannabidivarin is provided comprising preparing synthetically-prepared cannabidivarin, adding a solution of synthetically-prepared cannabidivarin in a suitable solvent to an antisolvent, removing some or all of the suitable solvent and crystallizing cannabidivarin from the solvent and antisolvent.

BRIEF DESCRIPTION OF THE DRAWINGS

FIG. 2 is an x-ray powder diffraction pattern of the region from about 8.5°2Θ to about 26.5°2Θ of (R,R)-(−)-crystalline cannabidivarin prepared with seeding.

DETAILED DESCRIPTION

Figure 1:
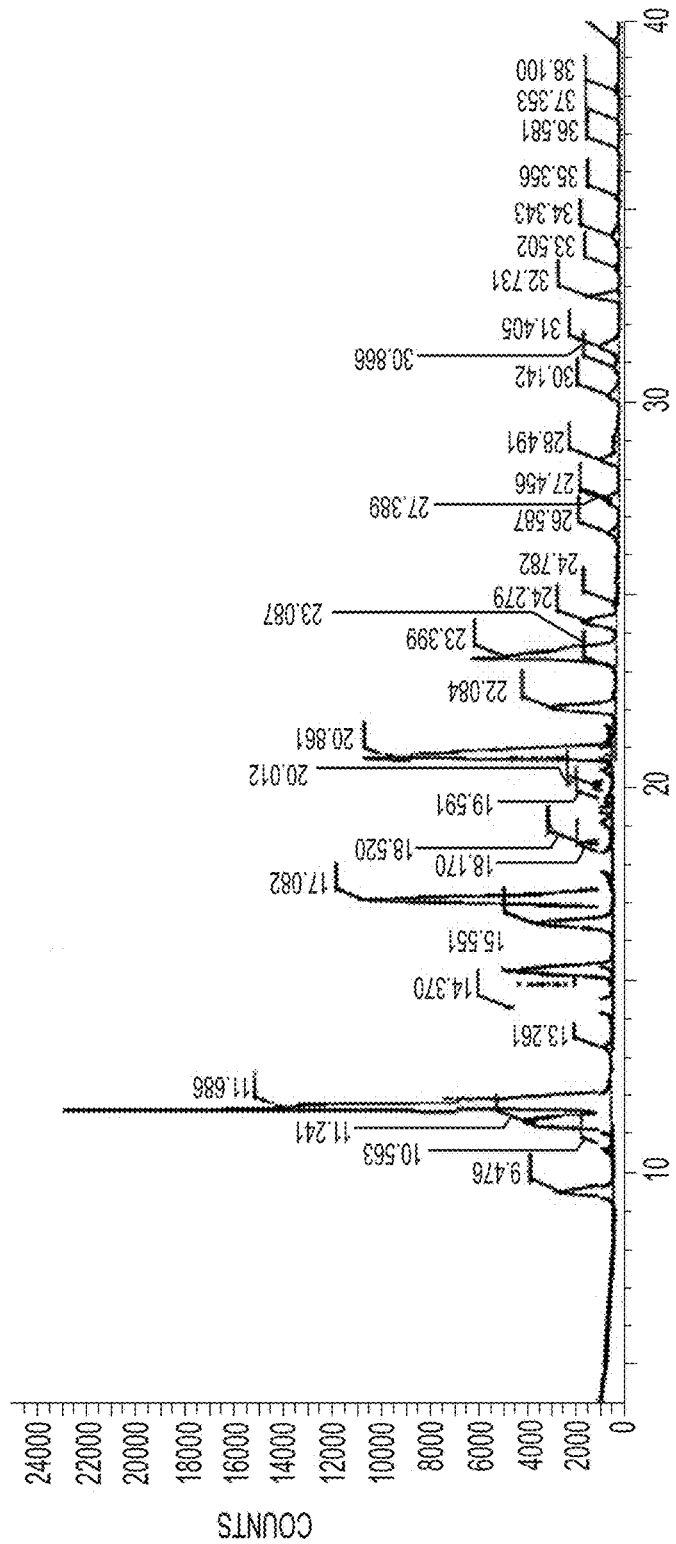
FIG. 1 is an x-ray powder diffraction pattern of (R,R)-(−)-crystalline cannabidivarin.
Figure 1A:
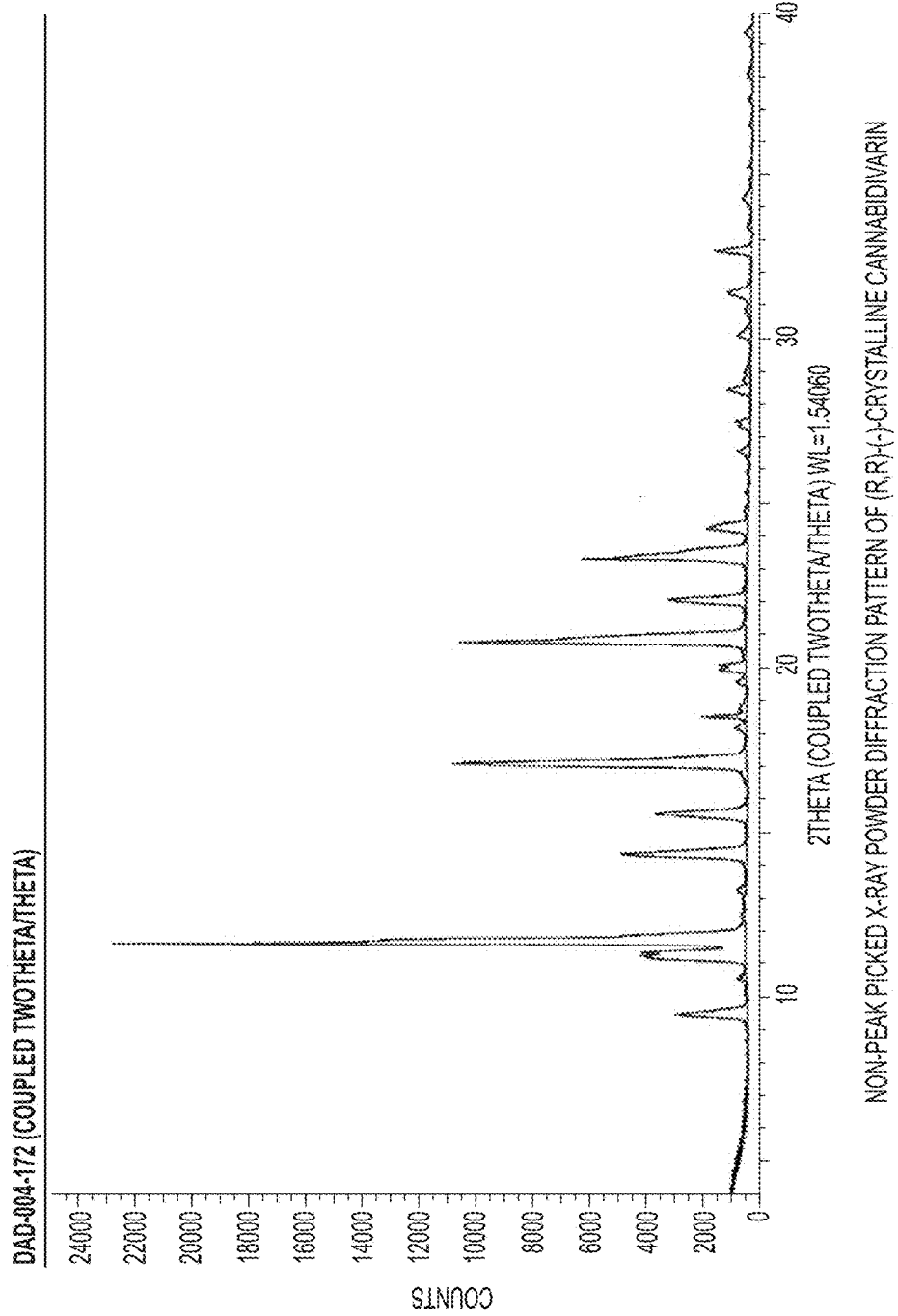
FIG. 1A is a non-peak picked x-ray powder diffraction pattern of (R,R)-(−)-crystalline cannabidivarin.

The term "crystalline form" is often used to refer to a class or type of solid-state material which is crystalline as that term is commonly understood by those of skill in the pharmaceutical arts. Crystalline forms of compounds, such as active pharmaceutical ingredients, are often preferred over amorphous or other non-crystalline forms because of properties such as stability, ease of preparation and use, and ease of purification.

When using solid-state analytical methods to characterize crystalline forms, such methods typically rely on other information about the chemical identity of the form. For example, solution-state methods such as HPLC, and solution-state NMR as well as knowledge about starting materials and chemical synthesis procedures can supply sufficient information to identify the chemical composition of a material. Solution-state techniques are not used to characterize crystalline forms. To determine whether a material is crystalline, one can use thermal methods, x-ray diffraction, light microscopy or visual observation, for example.

Crystalline forms may also be characterized by reference to various techniques. Examples of solid-state techniques which may be used to characterize and/or analyze crystalline forms include x-ray powder diffraction ("XRPD"), thermal techniques such as differential scanning calorimetry ("DSC") and melting point with, for example, a melting point apparatus, and infrared spectroscopy, such as Fourier-Transform infrared spectroscopy ("FT-IR").

Those of ordinary skill in the art will recognize that there are often multiple ways, including multiple ways using the same analytical technique, to characterize crystalline forms. For example, one may find that a single x-ray powder diffraction peak may be used to characterize a crystalline form. Additional peaks could also be used, but are not necessary, to characterize such forms including an entire diffraction pattern. Although all the peaks within an entire diffractogram may be used to characterize a crystalline form, one may instead, and typically does, as disclosed herein, use a subset of that data to characterize such a crystalline form.

X-ray powder diffraction patterns are some of the most commonly used solid-state analytical techniques to characterize crystalline forms. An x-ray powder diffraction pattern is an x-y graph with °2Θ (diffraction angle) on the x-axis and intensity on the y-axis. The peaks within this plot may be used to characterize a crystalline form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize crystalline forms.

As with any data measurement, there may be variability in x-ray powder diffraction data. In addition to the variability in peak intensity, there may be variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline form when prepared under different conditions may yield slightly different diffractograms. Factors such as particle size, moisture content, solvent content, and crystal orientation may all affect how a sample diffracts x-rays. Another source of variability comes from varying instrument parameters among different x-ray diffractometers. Likewise, different software packages process x-ray data differently, and this also leads to variability. These and other sources of variability are known to those of ordinary skill in the pharmaceutical arts.

Due to such sources of variability, it is common to recite x-ray diffraction peaks using the word "about" prior to the peak value in degrees two theta which presents the data to within ±0.1 or ±0.2°2Θ of the stated peak value depending on the circumstances. All x-ray powder diffraction peaks cited herein have been reported with a variability on the order of ±0.2°2Θ whether modified with the term "about" or not.

Infrared spectroscopy, such as FT-IR, is another technique that may be used to characterize crystalline forms together with, or separately from, x-ray powder diffraction and/or other techniques. In an infrared spectrum, absorbed light is plotted on the x-axis of a graph in the units of "wavenumber" ($cm^{-1}$), with intensity on the y-axis. Variation in the position of the peaks also exists and may be due to sample conditions as well as data collection and processing. The typical variability in such spectra reported herein is on the order of ±2.0 $cm^{-1}$. Thus, the use of the word "about" when referencing infrared peaks is meant to include this variability and all infrared peaks disclosed herein are intended to be reported with such variability whether modified with the term "about" or not.

Thermal methods are often used to characterize crystalline forms. The melting point of a crystalline form, as measured by methods such as capillary melting point, DSC, or hot stage microscopy, alone or in combination with techniques such as x-ray powder diffraction, infrared spectroscopy, or both, may be used to characterize crystalline forms.

As with any analytical technique, melting point determinations are also subject to variability. Common sources of variability, in addition to instrumental variability, are due to colligative properties such as the presence of other crystalline forms or other impurities within a sample whose melting point is being measured. Other sources of variability include the rate of heating, and techniques used for measuring the melting point.

Figure 2A:
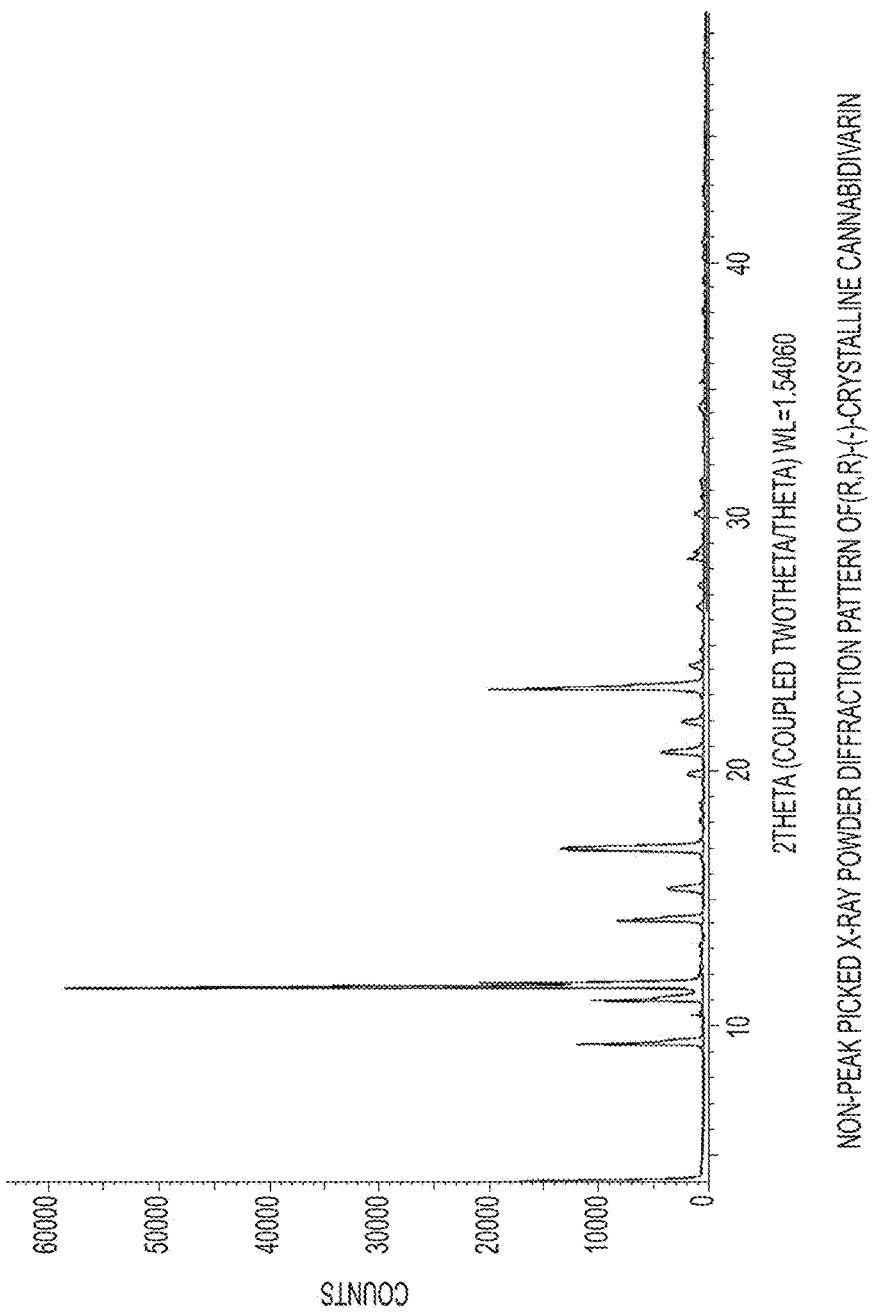
FIG. 2A is a non-peak picked x-ray powder diffraction pattern of (R,R)-(−)-crystalline cannabidivarin.
Figure 3:
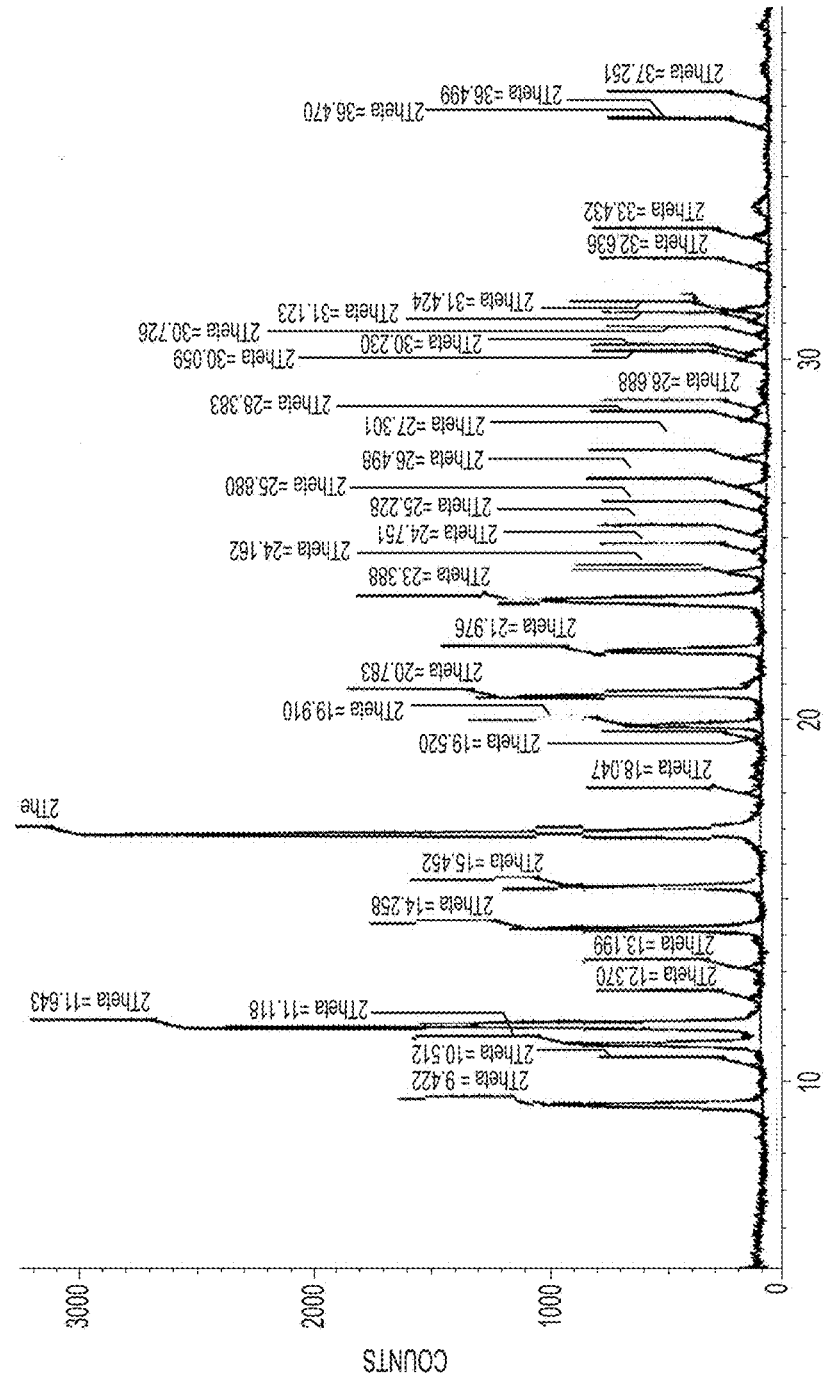
FIG. 3 is an x-ray powder diffraction pattern of (R,R)-(−)-crystalline cannabidivarin.

X-ray powder diffraction patterns corresponding to (R,R)-(−)-crystalline cannabidivarin can be found in FIGS. 1, 1A, 2, 2A, 3, and 3A with FIGS. 1, 2, and 3 being peak picked. The preparation of the sample of (R,R)-(−)-crystalline cannabidivarin for FIG. 1 can be found at Example 7. FIG. 2 is an expanded portion of an x-ray powder diffraction pattern corresponding to (R,R)-(−)-crystalline cannabidivarin made according to Example 8. FIG. 3 is (R,R)-(−)-crystalline cannabidivarin prepared according to Examples 2-5, with the last synthetic and crystallization steps set forth in Example 5.

Example 6 illustrates a non-crystalline preparation of (R,R)-(−)-cannabidivarin whereas Example 7 illustrates a preparation that provided a seed crystal of (R,R)-(−)-crystalline cannabidivarin after extensive chromatographic purification. In Example 8, (R,R)-(−)-crystalline cannabidivarin was generated by seeding the product of Example 6 with seed crystals from Example 7. By comparison, in another preparation, (R,R)-(−)-crystalline cannabidivarin in Example 5 was made without the need for extensive chromatography or the use of seed crystals. Seeding is a phenomenon whereby solid particles, often of the material sought to be crystallized, are added to a crystallization process to induce crystallization. Seeding with (R,R)-(−)-crystalline cannabidivarin may be used to help facilitate the crystallization of (R,R)-(−)-crystalline cannabidivarin. In other embodiments, (R,R)-(−)-crystalline cannabidivarin may be prepared without the use of such seed crystals. Seeds may also be used to form crystals from natural extracts of cannabidivarin prepared by methods of the prior art. For example, cannabidivarin extract is soluble in heptane and can be seeded with solid cannabidivarin, such as crystalline cannabidivarin, to cause crystalline cannabidivarin to form which then may be isolated after filtration.

In many embodiments of the invention, a substantially pure (R,R)-(−)-cannabidivarin is provided. By "substantially pure" what is meant with respect to (R,R)-(−)-cannabidivarin is (R,R)-(−)-cannabidivarin having a stereochemical purity of at least 90% wherein the amount of diastereomers of cannabidivarin, the (S,S)-(+)-cannabidivarin enantiomer of cannabidivarin and racemic cannabidivarin is present at less than 10% in total. In other embodiments, such stereochemical purity is at least 91%, 92%, 93%, 94%, 95%, 96%, 97%, 98%, or 99%. Similarly, substantially pure (R,R)-(−)-crystalline cannabidivarin is provided wherein "substantially pure" means (R,R)-(−)-crystalline cannabidivarin having a stereochemical purity of at least 90% wherein the amount of diastereomers of cannabidivarin, the (S,S)-(+)-crystalline cannabidivarin enantiomer and racemic cannabidivarin is present at less than 10% in total. In other embodiments, such stereochemical purity is at least 91%, 92%, 93%, 94%, 95%, 96%, 97%, 98%, or 99%. The terms "substantially pure forms" refers to substantially pure (R,R)-(−)-crystalline cannabidivarin and substantially pure (S,S)-

(+)-crystalline cannabidivarin. By controlling the stereochemical purity, one may combine various enantiomers and diastereomers of cannabidivarin to obtain mixtures of a given stereochemical purity. For example, one can combine a 50/50 mix of about 90% (S,S)-(+) cannabidivarin enantiomer together with racemic cannabidivarin to obtain cannabidivarin that is about 45% (S,S)-(+) cannabidivarin. Such may be done with solid cannabidivarin such as crystalline cannabidivarin of the invention.

Figure 3A:
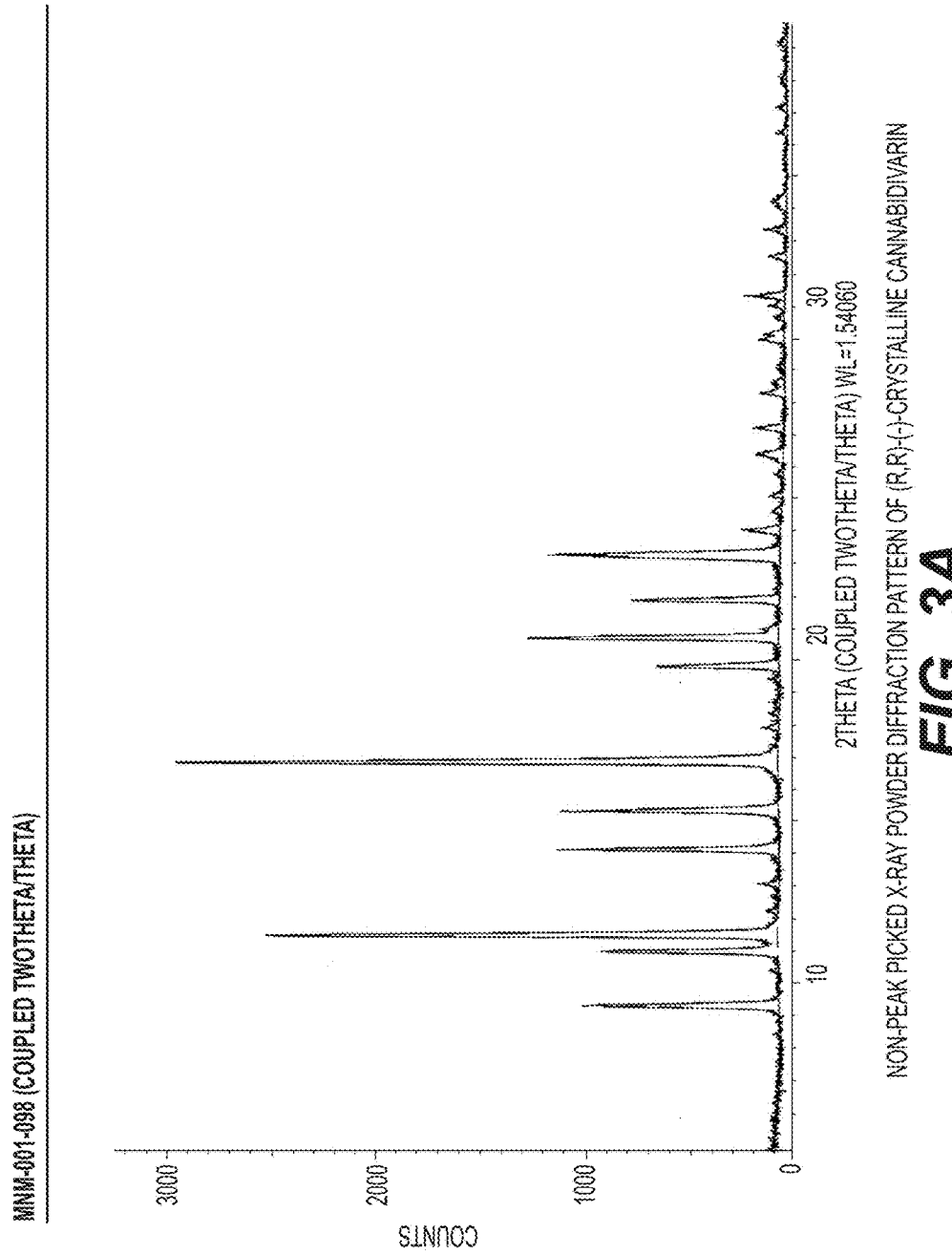
FIG. 3A is a non-peak picked x-ray powder diffraction pattern of (R,R)-(−)-crystalline cannabidivarin.

In each of FIGS. 1-3, the x-axis positions of the peaks in the powder x-ray diffraction patterns have been identified, and tables 3-5 list the peaks for each corresponding diffraction pattern. In many embodiments of the invention, (R,R)-(−)-crystalline cannabidivarin may be characterized by one or more of the peaks set forth in FIG. 1, FIG. 2, or FIG. 3. For example, a peak at about 9.4°2Θ in the powder x-ray diffraction pattern may be used to characterize (R,R)-(−)-crystalline cannabidivarin. In FIG. 1, there is a peak at about 9.5°2Θ, in FIGS. 2 and 3 the corresponding peak is at about 9.4°2Θ. Averaging these values yields a peak at about 9.4°2Θ. In still another example, a peak at about 11.7°2Θ may be used to characterize (R,R)-(−)-crystalline cannabidivarin (averaging about 11.7°2Θ, 11.8°2Θ, and 11.6°2Θ). In other embodiments, more than one peak may be used to characterize (R,R)-(−)-crystalline cannabidivarin. For example, one or more peaks at about 14.4°2Θ, 15.5°2Θ, or 17.1°2Θ may be used to characterize (R,R)-(−)-crystalline cannabidivarin. In other embodiments, one or more peaks at about 9.4°2Θ, 10.5°2Θ, 11.7°2Θ, 14.4°2Θ, 15.5°2Θ, or 17.1°2Θ may be used to characterize (R,R)-(−)-crystalline cannabidivarin. In another embodiment, a diffraction pattern substantially the same as FIG. 1A. FIG. 2A or FIG. 3A may be used to characterize (R,R)-(−)-crystalline cannabidivarin. Other peaks in the x-ray powder diffraction pattern of (R,R)-(−)-crystalline cannabidivarin may also be used to characterize this crystalline form.

Figure 4:
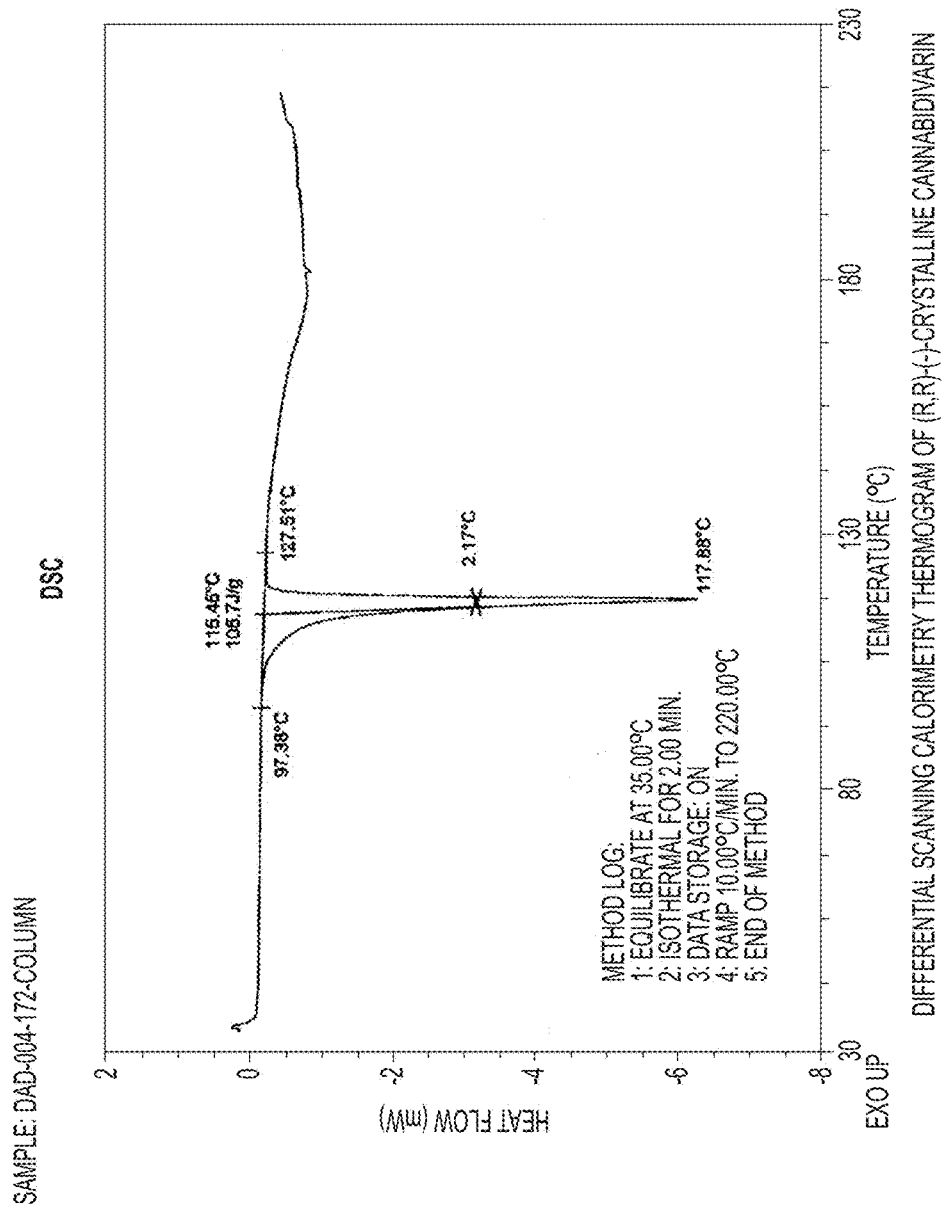
FIG. 4 is a differential scanning calorimetry thermogram of (R,R)-(−)-crystalline cannabidivarin.
Figure 5:
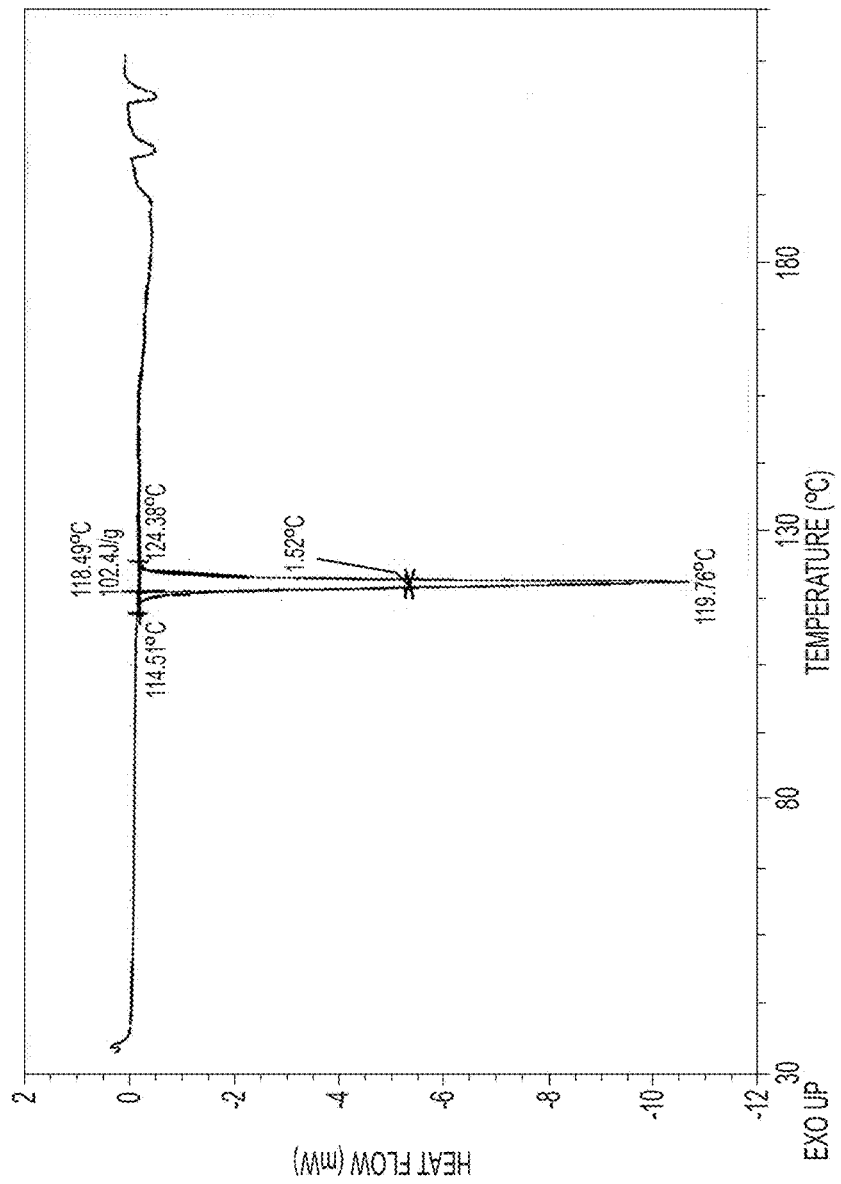
FIG. 5 is a differential scanning calorimetry thermogram of (R,R)-(−)-crystalline cannabidivarin prepared with seeding.
Figure 6:
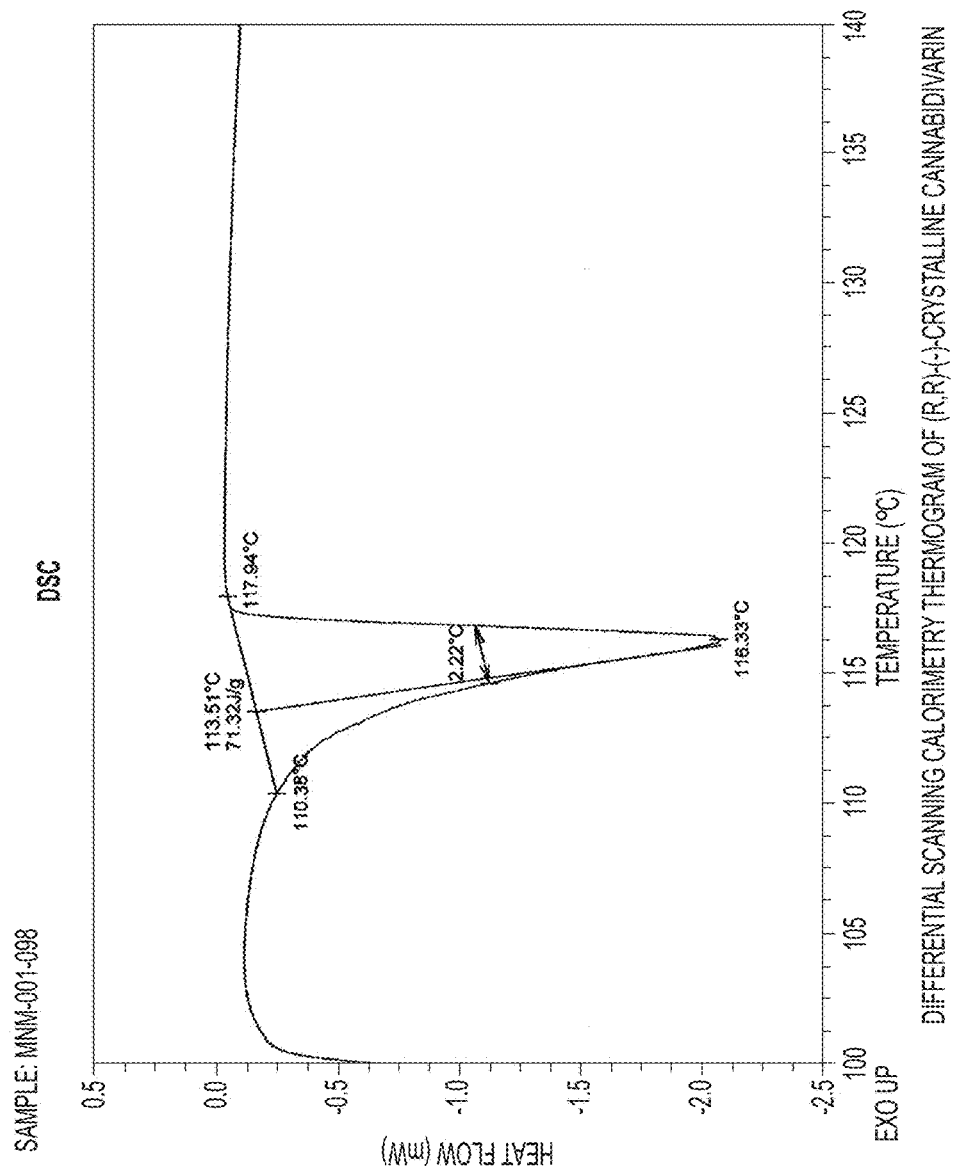
FIG. 6 is a differential scanning calorimetry thermogram of (R,R)-(−)-crystalline cannabidivarin.
Figure 7:
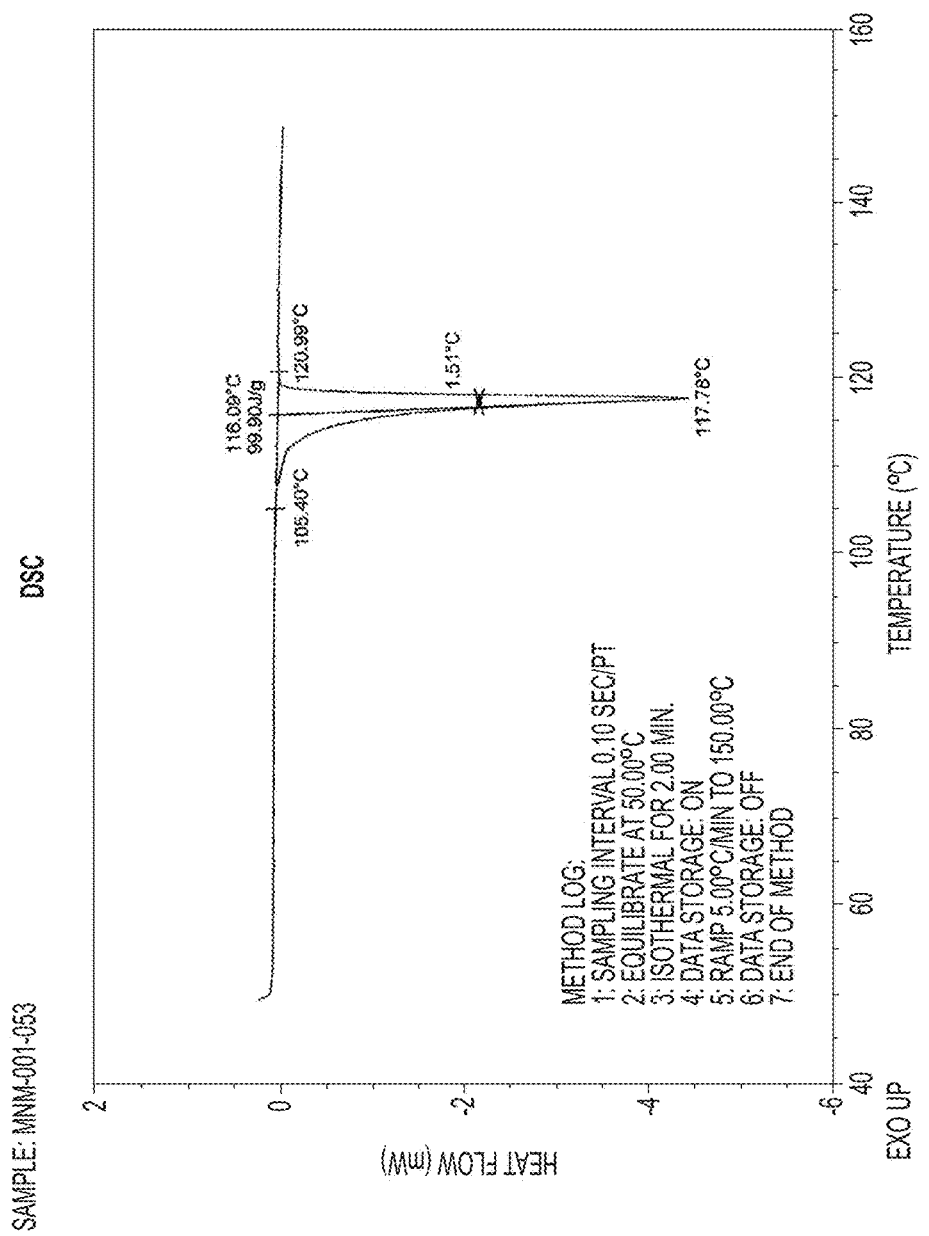
FIG. 7 is a differential scanning calorimetry thermogram of a different lot of (R,R)-(−)-crystalline cannabidivarin than shown in FIG. 6.

Thermal methods may also be used to characterize (R,R)-(−)-crystalline cannabidivarin alone or in conjunction with other analytical techniques. FIG. 4 is a differential scanning calorimetry thermogram of (R,R)-(−)-crystalline cannabidivarin prepared by Example 7. FIG. 5 is a differential scanning calorimetry thermogram of (R,R)-(−)-crystalline cannabidivarin prepared by Example 8. FIG. 6 is a differential scanning calorimetry thermogram of (R,R)-(−)-crystalline cannabidivarin prepared by Example 5. FIG. 7 is a differential scanning calorimetry thermogram of another lot of (R,R)-(−)-crystalline cannabidivarin.

In each thermogram at above 100° C., a single endotherm is present, consistent with the melt of a crystalline solid. In FIG. 4 and FIG. 5, a temperature ramp rate of 10° C. per minute was used starting at 35° C. all the way to 220° C. The peak maxima were recorded at about 118° C. and 120° C. respectively. By comparison, in FIG. 6, a ramp rate of 10° C. per minute was used from 40° C. to 100° C. and then slowed to 2° C. per minute until 140° C. when it was then increased to 10° C. per minute. A peak maximum at about 116° C. was recorded. In FIG. 7, a ramp rate of 5° C. per minute was used from 50° C. to 150° C. In FIG. 7, a peak maximum at about 118° C. was recorded. Thus, a peak maximum in a DSC thermogram endotherm at between about 116° C. and 120° C. may also be used to characterize (R,R)-(−)-crystalline cannabidivarin.

In other embodiments, the thermal characterizing data such as an endotherm onset, maximum, or both together, may be used with one or more peaks at about 9.4°2Θ, 10.5°2Θ, 11.7°2Θ, 14.4°2Θ, 15.5°2Θ, or 17.1°2Θ to characterize (R,R)-(−)-crystalline cannabidivarin. Thus, for example, an endotherm maximum at between about 116° C. and 120° C. together with an x-ray powder diffraction peak at about 9.4°2Θ may be used to characterize (R,R)-(−)-crystalline cannabidivarin.

Three synthetic and crystallization routes are disclosed herein in Examples 5, 7, and 8 respectively for making (R,R)-(−)-crystalline cannabidivarin. Each describes making (R,R)-(−)-cannabidivarin including (R,R)-(−)-crystalline cannabidivarin. Additionally, Example 6 describes another synthetic route for making (R,R)-(−)-cannabidivarin. A melting point was observed for each crystalline Example ranging from about 117° C.-119° C. for Example 5, about 118° C. for Example 7 and about 120° C. for Example 8. Thus, a melting point temperature of between about 117° C. and 120° C. may be used to characterize (R,R)-(−)-crystalline cannabidivarin. Melting point may be used alone or together with one or more analytical techniques to characterize (R,R)-(−)-crystalline cannabidivarin. For example, a melting point of between about 117° C. and 120° C. together with one or more peaks at about 9.4°2Θ, 10.5°2Θ, 11.7°2Θ, 14.4°2Θ, 15.5°2Θ, or 17.1°2Θ may be used to characterize (R,R)-(−)-crystalline cannabidivarin. Thus, for example, a melting point of between about 117° C. and 120° C. together with an x-ray powder diffraction peak at about 9.4°2Θ may be used to characterize (R,R)-(−)-crystalline cannabidivarin.

Figure 8:
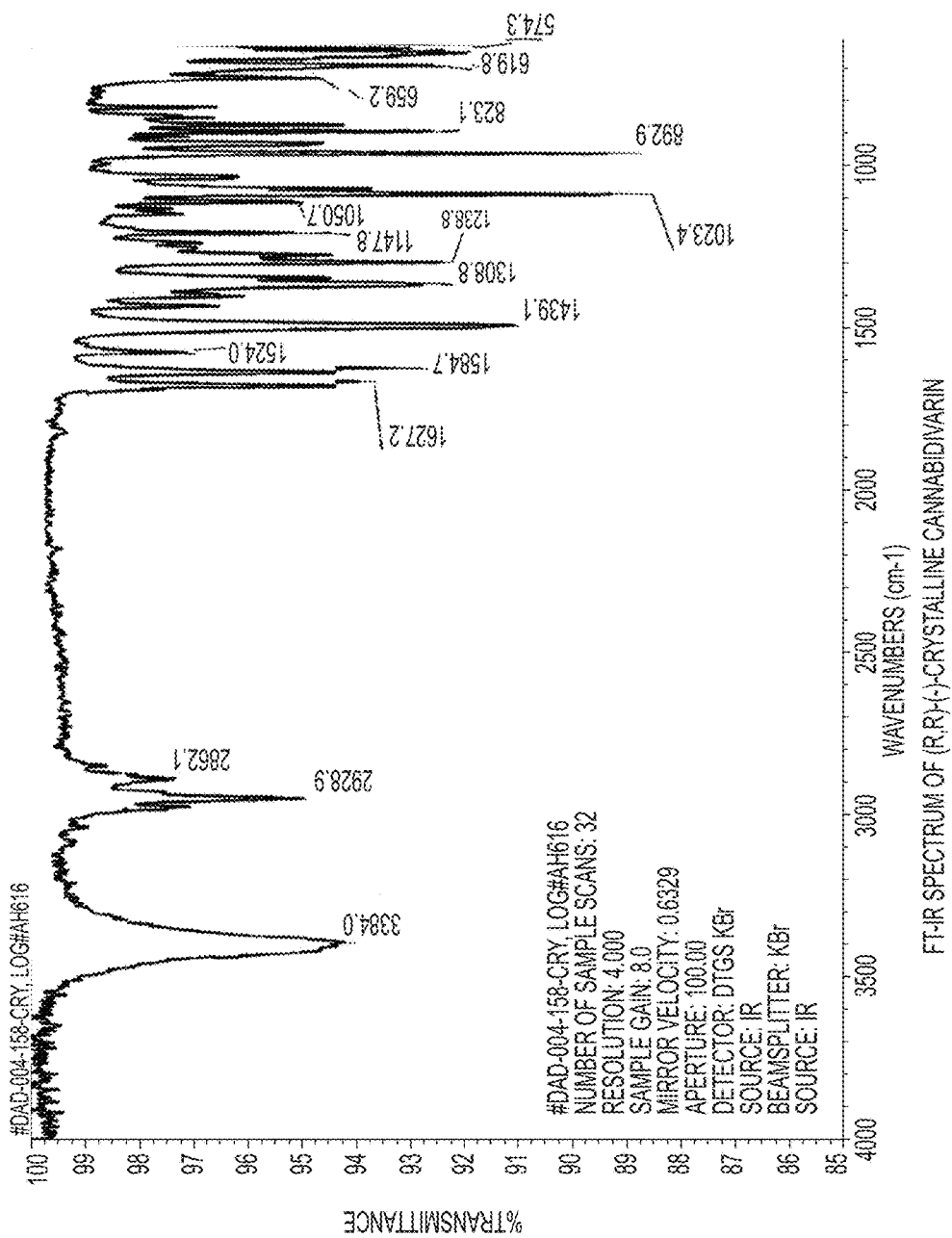
FIG. 8 is an FT-IR spectrum of (R,R)-(−)-crystalline cannabidivarin.
Figure 9:
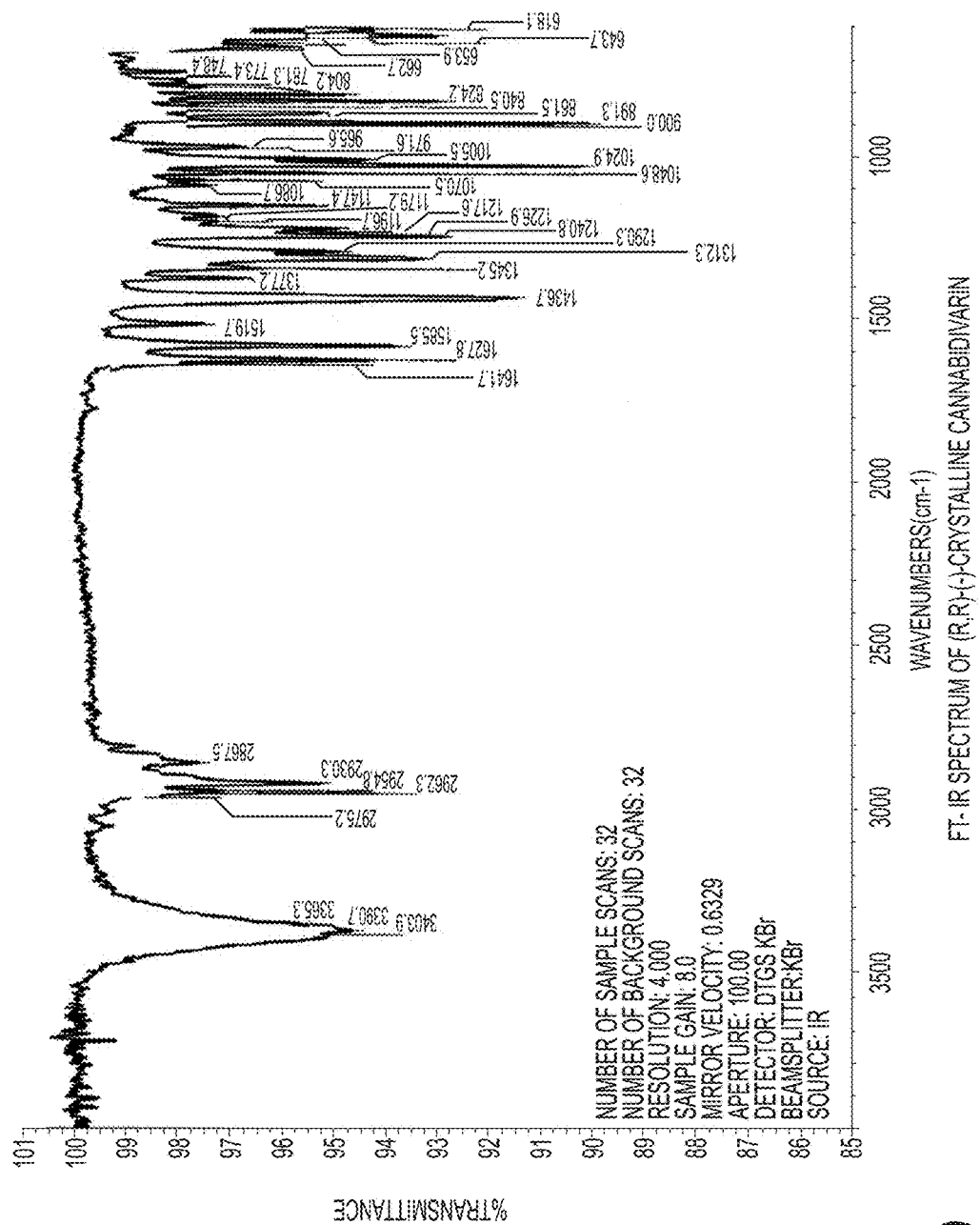
FIG. 9 is an FT-IR spectrum of a different lot of (R,R)-(−)-crystalline cannabidivarin than shown in FIG. 8.
Figure 10:
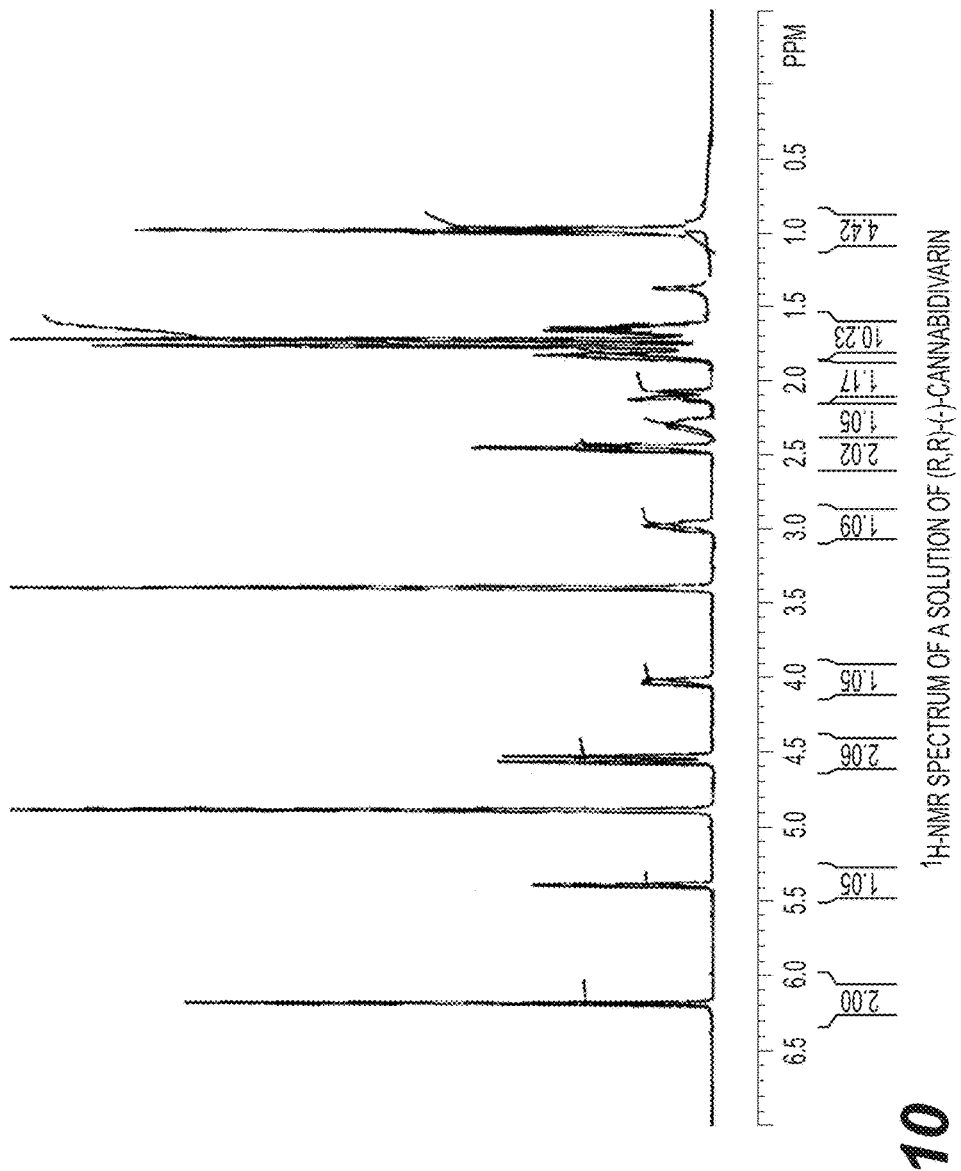
FIG. 10 is a $^1$H-NMR spectrum of a solution of (R,R)-(−)-cannabidivarin.
Figure 11:
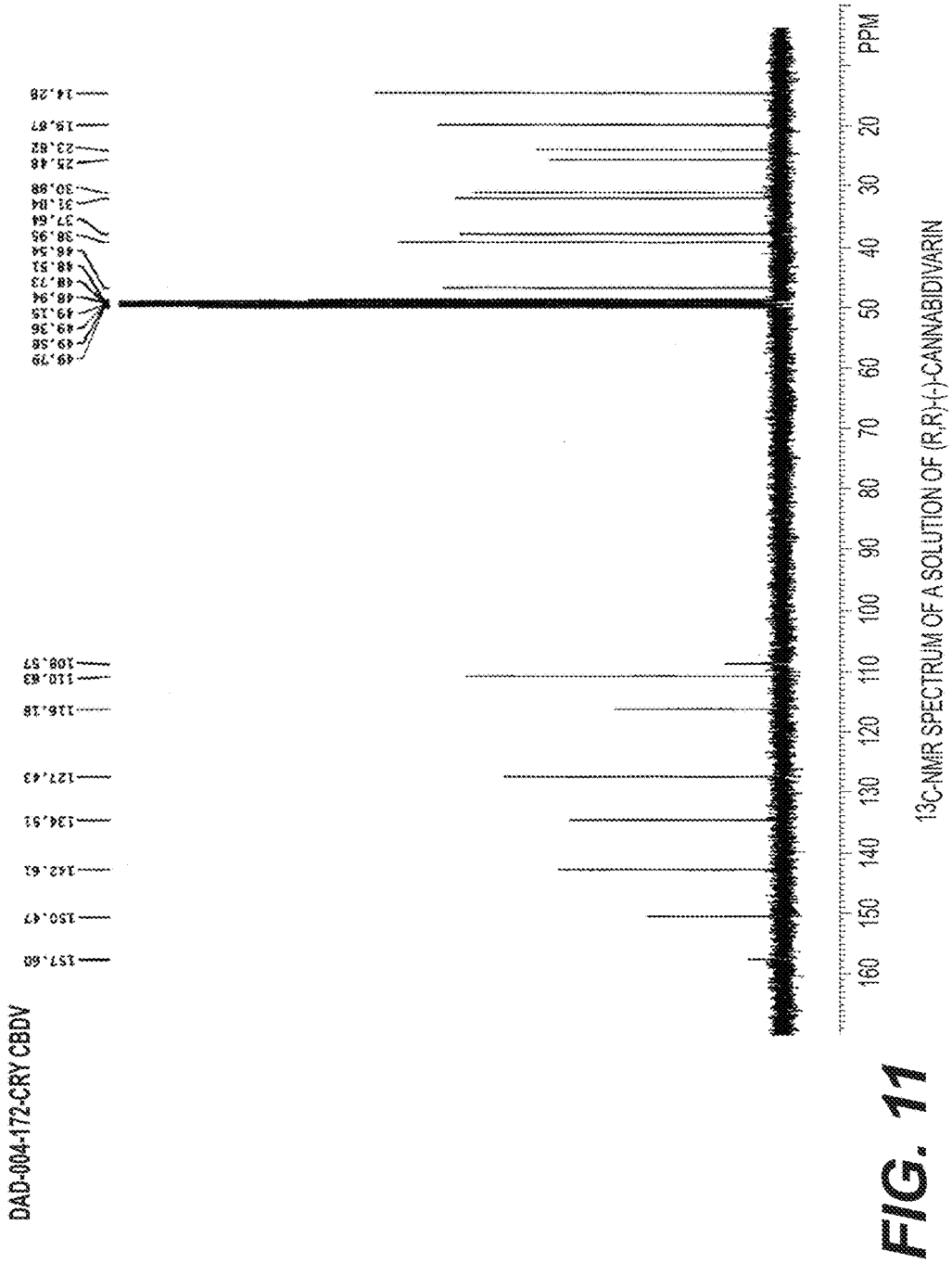
FIG. 11 is a $^{13}$C-NMR spectrum of a solution of (R,R)-(−)-cannabidivarin.

Turning to FIG. 8, for example, an FT-IR spectrum having one or more peaks at about 893 cm$^{-1}$, 1585 cm$^{-1}$, 1627 cm$^{-1}$ or 2929 cm$^{-1}$ may be used to characterize (R,R)-(−)-crystalline cannabidivarin. In other embodiments, such one or more FT-IR peaks may be used together with one or more peaks in the x-ray powder diffraction pattern of (R,R)-(−)-crystalline cannabidivarin such as at about 9.4°2Θ, 10.5°2Θ, 11.7°2Θ, 14.4°2Θ, 15.5°2Θ, or 17.1°2Θ to characterize (R,R)-(−)-crystalline cannabidivarin. In still other embodiments, one or more of said FT-IR peaks together with one or more of said x-ray powder diffraction peaks together with a melting point of between about 117° C. and 120° C. may be used to characterize (R,R)-(−)-crystalline cannabidivarin. In addition to the melting point, or in place thereof, one may also include a DSC endotherm peak maximum of between about 116° C. and 120° C. to characterize (R,R)-(−)-crystalline cannabidivarin. Thus, for example, a melting point of between about 117° C. and about 120° C. and a peak in the FT-IR spectrum of about 1585 cm$^{-1}$ may be used to characterize (R,R)-(−)-crystalline cannabidivarin. Further, the FT-IR peaks disclosed herein may be used in combination with both x-ray diffraction data and thermal data set forth herein to characterize (R,R)-(−)-crystalline cannabidivarin. Thus, for example an FT-IR peak at about 1627 cm$^{-1}$, together with a DSC endotherm peak maximum at between about 116° C. and 120° C., together with an x-ray powder diffraction peak at about 11.7°2Θ may be used to characterize (R,R)-(−)-crystalline cannabidivarin.

A process for preparing (R,R)-(−)-cannabidivarin is set forth below:

Preparation of (R,R)-(-)-Cannabidivarin

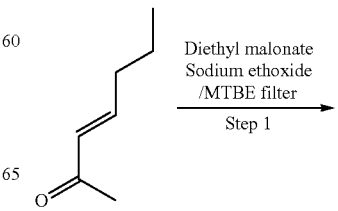

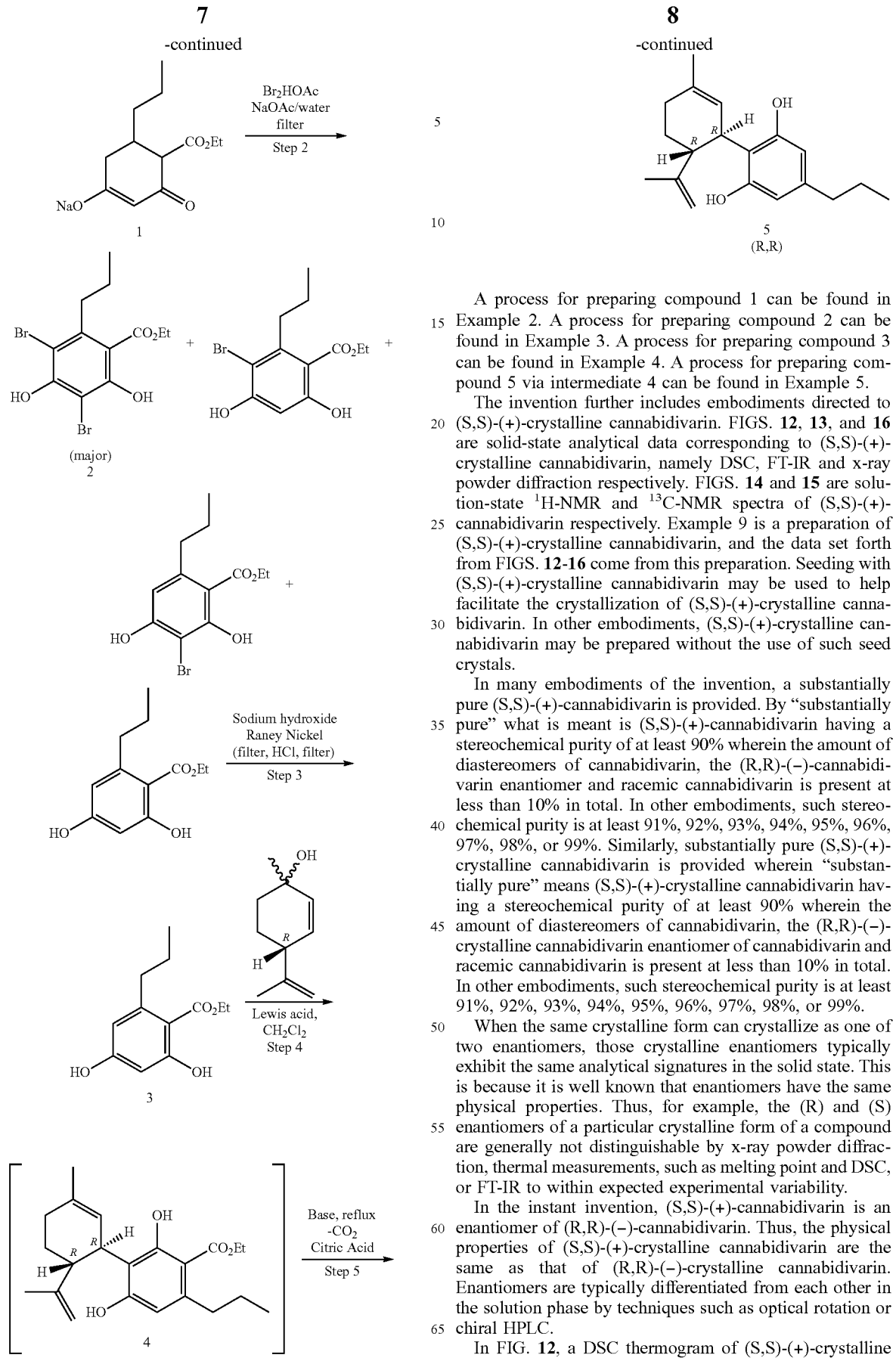

A process for preparing compound 1 can be found in Example 2. A process for preparing compound 2 can be found in Example 3. A process for preparing compound 3 can be found in Example 4. A process for preparing compound 5 via intermediate 4 can be found in Example 5.

Figure 12:
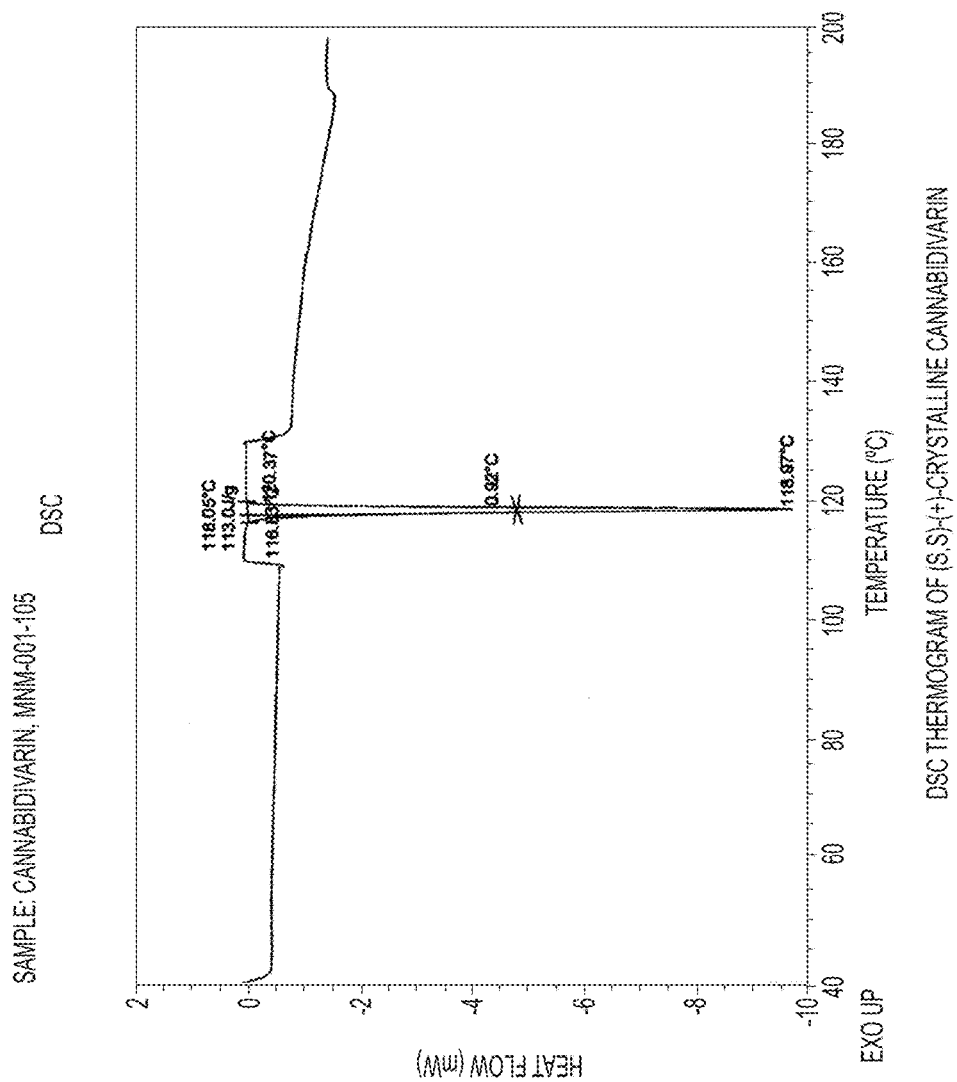
FIG. 12 is a differential scanning calorimetry thermogram of (S,S)-(+)-crystalline cannabidivarin.
Figure 13:
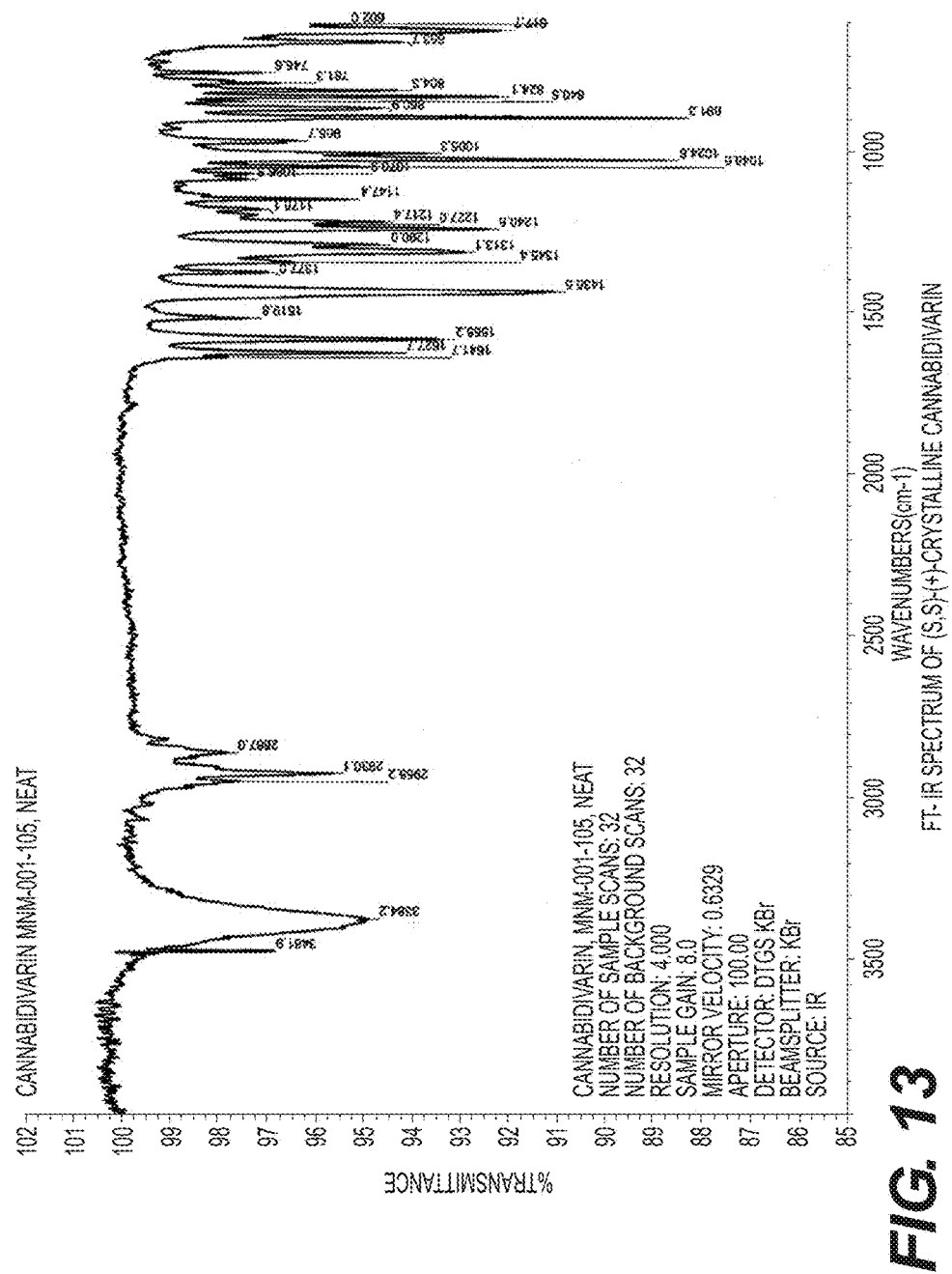
FIG. 13 is an FT-IR spectrum of (S,S)-(+)-crystalline cannabidivarin.
Figure 14:
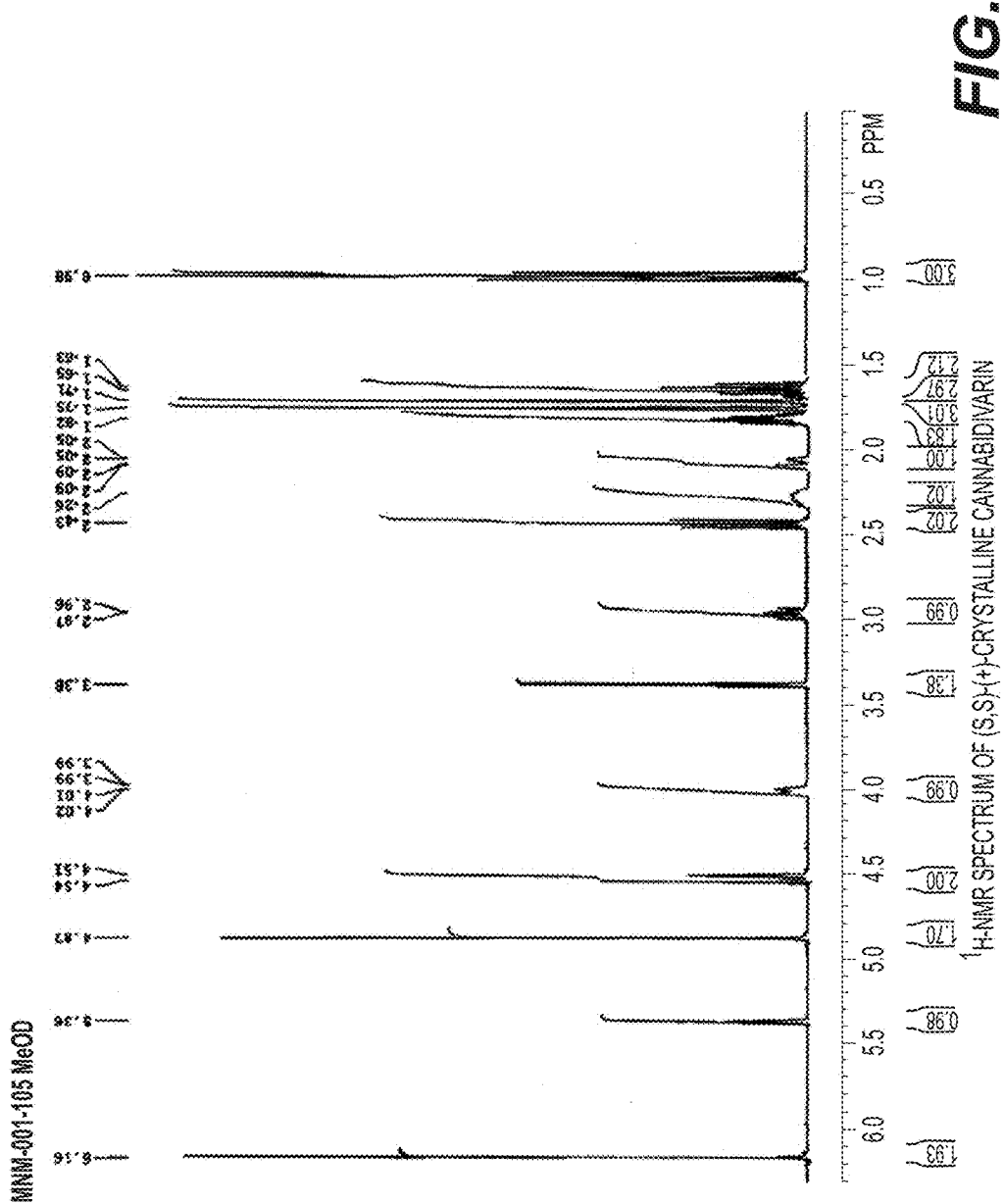
FIG. 14 is a $^1$H-NMR spectrum of (S,S)-(+)-crystalline cannabidivarin.
Figure 15:
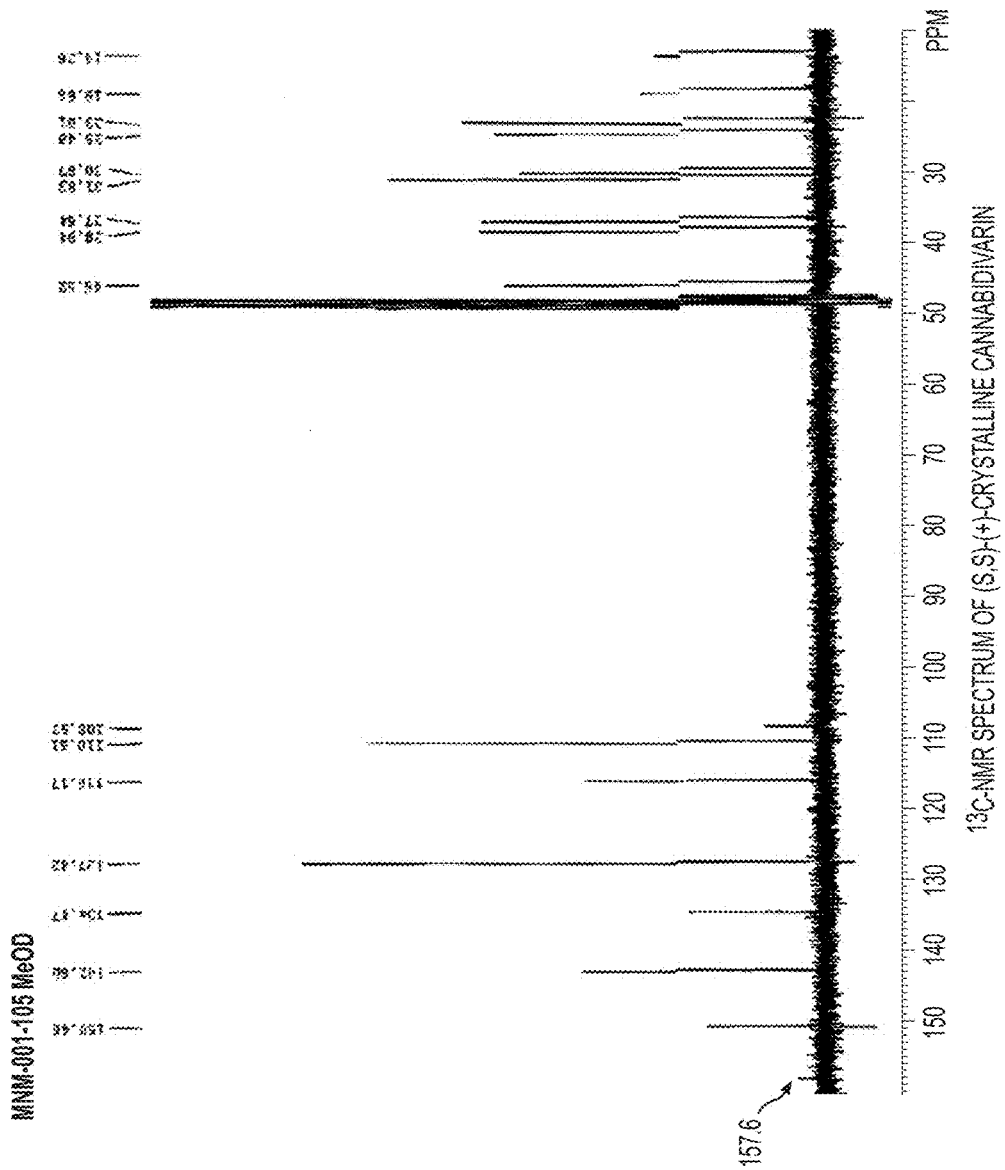
FIG. 15 is a $^{13}$C-NMR spectrum of a (S,S)-(+)-crystalline cannabidivarin.
Figure 16:
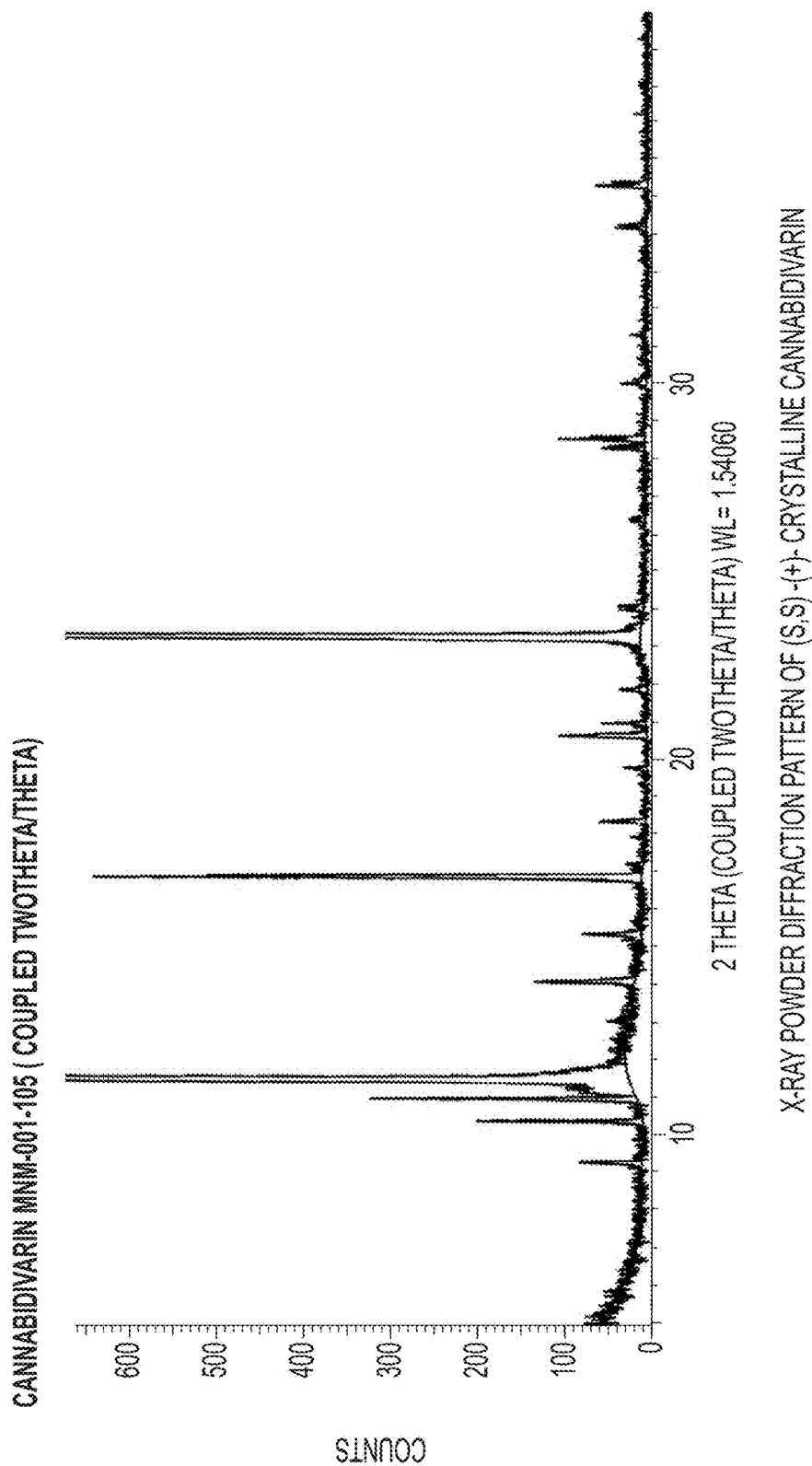
FIG. 16 is an x-ray powder diffraction pattern of (S,S)-(+)-crystalline cannabidivarin.

The invention further includes embodiments directed to (S,S)-(+)-crystalline cannabidivarin. FIGS. 12, 13, and 16 are solid-state analytical data corresponding to (S,S)-(+)-crystalline cannabidivarin, namely DSC, FT-IR and x-ray powder diffraction respectively. FIGS. 14 and 15 are solution-state $^1$H-NMR and $^{13}$C-NMR spectra of (S,S)-(+)-cannabidivarin respectively. Example 9 is a preparation of (S,S)-(+)-crystalline cannabidivarin, and the data set forth from FIGS. 12-16 come from this preparation. Seeding with (S,S)-(+)-crystalline cannabidivarin may be used to help facilitate the crystallization of (S,S)-(+)-crystalline cannabidivarin. In other embodiments, (S,S)-(+)-crystalline cannabidivarin may be prepared without the use of such seed crystals.

In many embodiments of the invention, a substantially pure (S,S)-(+)-cannabidivarin is provided. By "substantially pure" what is meant is (S,S)-(+)-cannabidivarin having a stereochemical purity of at least 90% wherein the amount of diastereomers of cannabidivarin, the (R,R)-(−)-cannabidivarin enantiomer and racemic cannabidivarin is present at less than 10% in total. In other embodiments, such stereochemical purity is at least 91%, 92%, 93%, 94%, 95%, 96%, 97%, 98%, or 99%. Similarly, substantially pure (S,S)-(+)-crystalline cannabidivarin is provided wherein "substantially pure" means (S,S)-(+)-crystalline cannabidivarin having a stereochemical purity of at least 90% wherein the amount of diastereomers of cannabidivarin, the (R,R)-(−)-crystalline cannabidivarin enantiomer of cannabidivarin and racemic cannabidivarin is present at less than 10% in total. In other embodiments, such stereochemical purity is at least 91%, 92%, 93%, 94%, 95%, 96%, 97%, 98%, or 99%.

When the same crystalline form can crystallize as one of two enantiomers, those crystalline enantiomers typically exhibit the same analytical signatures in the solid state. This is because it is well known that enantiomers have the same physical properties. Thus, for example, the (R) and (S) enantiomers of a particular crystalline form of a compound are generally not distinguishable by x-ray powder diffraction, thermal measurements, such as melting point and DSC, or FT-IR to within expected experimental variability.

In the instant invention, (S,S)-(+)-cannabidivarin is an enantiomer of (R,R)-(−)-cannabidivarin. Thus, the physical properties of (S,S)-(+)-crystalline cannabidivarin are the same as that of (R,R)-(−)-crystalline cannabidivarin. Enantiomers are typically differentiated from each other in the solution phase by techniques such as optical rotation or chiral HPLC.

In FIG. 12, a DSC thermogram of (S,S)-(+)-crystalline cannabidivarin shows an endotherm with a peak maximum at about 119° C. with a ramp rate of 2° per minute from about 110° C. to about 130° C. (otherwise 10° C. per minute). These data are within experimental variation of what is reported for (R,R)-(−)-crystalline cannabidivarin herein. Likewise, the melting point of (R,R)-(−)-crystalline cannabidivarin is between about 117° C. and 120° C. whereas the melting point of (S,S)-(+)-crystalline cannabidivarin was measured to be 119° C.

In FIG. 13, an FT-IR spectrum of (S,S) is provided. The corresponding peaks in FIG. 13 and FIG. 6 are as follows in Table 1.

TABLE 1

| (S,S)-(+)-crystalline cannabidivarin | (R,R)-(−)-crystalline cannabidivarin | Difference |
|---|---|---|
| 891 cm$^{-1}$ | 893 cm$^{-1}$ | 2 cm$^{-1}$ |
| 1585 cm$^{-1}$ | 1585 cm$^{-1}$ | 0 cm$^{-1}$ |
| 1627 cm$^{-1}$ | 1628 cm$^{-1}$ | 1 cm$^{-1}$ |
| 2930 cm$^{-1}$ | 2929 cm$^{-1}$ | 1 cm$^{-1}$ |

The average difference between the peaks is about 1 cm$^{-1}$ which is within expected experimental variability.

In addition, the x-ray powder diffraction patterns of (R,R)-(−)-crystalline cannabidivarin and (S,S)-(+)-crystalline cannabidivarin are not distinguishable. Table 1 below shows measured values of both materials from the figures:

TABLE 2

| (S,S)-(+)-crystalline cannabidivarin | (R,R)-(−)-crystalline cannabidivarin | Difference |
|---|---|---|
| 11.6 | 11.7 | 0.1 |
| 9.4 | 9.4 | 0 |
| 10.5 | 10.5 | 0 |
| 16.9 | 17.1 | 0.2 |
| 14.2 | 14.4 | 0.2 |
| 15.4 | 15.5 | 0.1 |

No peak differs by more than 0.2 and the average difference among all six reported peaks is about 0.1°2Θ.

Tables 3, 4, 5, and 6 are the peak lists corresponding to FIGS. (1,1A), (2,2A), (3,3A) and 16 respectively.

TABLE 3

| Index | Angle | d Value | Rel. Intensity |
|---|---|---|---|
| 0 | 35.356 | 2.53668 | 0.3% |
| 1 | 36.581 | 2.45446 | 0.6% |
| 2 | 23.087 | 3.84928 | 0.6% |
| 3 | 38.100 | 2.36001 | 0.9% |
| 4 | 37.353 | 2.40552 | 1.0% |
| 5 | 24.782 | 3.58972 | 1.0% |
| 6 | 33.502 | 2.67270 | 1.1% |
| 7 | 30.866 | 2.89467 | 1.5% |
| 8 | 10.563 | 8.36835 | 1.5% |
| 9 | 39.415 | 2.28425 | 1.9% |
| 10 | 27.456 | 3.24598 | 2.2% |
| 11 | 13.261 | 6.67102 | 2.3% |
| 12 | 34.343 | 2.60909 | 2.4% |
| 13 | 27.389 | 3.25375 | 2.6% |
| 14 | 18.170 | 4.87848 | 2.8% |
| 15 | 26.587 | 3.35000 | 2.9% |
| 16 | 19.591 | 4.52770 | 2.9% |
| 17 | 30.142 | 2.96250 | 3.4% |
| 18 | 20.012 | 4.43327 | 5.6% |
| 19 | 31.405 | 2.84620 | 5.8% |
| 20 | 28.491 | 3.13034 | 5.9% |
| 21 | 24.279 | 3.66306 | 8.8% |
| 22 | 32.731 | 2.73382 | 9.4% |
| 23 | 18.520 | 4.78703 | 11.5% |

TABLE 3-continued

| Index | Angle | d Value | Rel. Intensity |
|---|---|---|---|
| 24 | 9.476 | 9.32543 | 17.6% |
| 25 | 22.084 | 4.02182 | 19.3% |
| 26 | 15.551 | 5.69355 | 24.2% |
| 27 | 11.241 | 7.86506 | 27.3% |
| 28 | 14.370 | 6.15895 | 32.3% |
| 29 | 23.399 | 3.79865 | 34.1% |
| 30 | 20.861 | 4.25471 | 65.9% |
| 31 | 17.082 | 5.18650 | 75.4% |
| 32 | 11.686 | 7.56666 | 100.0% |

TABLE 4

| Index | Angle | d Value | Rel. Intensity |
|---|---|---|---|
| 0 | 8.488 | 10.40944 | 0.3% |
| 1 | 9.397 | 9.40388 | 19.8% |
| 2 | 10.021 | 8.82014 | 0.4% |
| 3 | 10.500 | 8.41805 | 1.8% |
| 4 | 10.646 | 8.30306 | 0.5% |
| 5 | 11.099 | 7.96566 | 17.8% |
| 6 | 11.191 | 7.89999 | 7.5% |
| 7 | 11.628 | 7.60406 | 100.0% |
| 8 | 11.778 | 7.50795 | 34.4% |
| 9 | 13.226 | 6.68879 | 0.5% |
| 10 | 14.254 | 6.20882 | 13.5% |
| 11 | 14.372 | 6.15813 | 6.8% |
| 12 | 15.520 | 5.70476 | 5.7% |
| 13 | 17.041 | 5.19913 | 22.7% |
| 14 | 17.089 | 5.18464 | 21.5% |
| 15 | 18.091 | 4.89953 | 0.6% |
| 16 | 18.117 | 4.89260 | 0.6% |
| 17 | 18.832 | 4.70834 | 0.7% |
| 18 | 19.942 | 4.44874 | 2.6% |
| 19 | 19.990 | 4.43815 | 2.5% |
| 20 | 20.820 | 4.26317 | 6.5% |
| 21 | 20.855 | 4.25601 | 6.8% |
| 22 | 20.903 | 4.24639 | 5.6% |
| 23 | 22.060 | 4.02612 | 3.6% |
| 24 | 23.339 | 3.80839 | 33.2% |
| 25 | 23.385 | 3.80097 | 24.6% |
| 26 | 23.468 | 3.78766 | 11.8% |
| 27 | 24.246 | 3.66784 | 2.2% |
| 28 | 24.231 | 3.67020 | 2.2% |
| 29 | 24.800 | 3.58725 | 0.5% |
| 30 | 25.315 | 3.51542 | 0.3% |
| 31 | 27.317 | 3.26216 | 0.8% |
| 32 | 27.505 | 3.24021 | 0.2% |
| 33 | 27.355 | 3.25771 | 0.9% |
| 34 | 28.386 | 3.14171 | 2.5% |
| 35 | 28.449 | 3.13486 | 2.0% |
| 36 | 28.668 | 3.11135 | 1.7% |
| 37 | 28.739 | 3.10388 | 1.2% |
| 38 | 30.170 | 2.95985 | 1.5% |
| 39 | 30.751 | 2.90518 | 0.4% |
| 40 | 30.826 | 2.89830 | 0.6% |
| 41 | 31.468 | 2.84066 | 0.7% |
| 42 | 33.641 | 2.66198 | 0.3% |
| 43 | 35.302 | 2.54043 | 0.7% |
| 44 | 35.391 | 2.53426 | 0.4% |
| 45 | 39.309 | 2.29020 | 0.3% |
| 46 | 40.300 | 2.23614 | 0.4% |
| 47 | 40.276 | 2.23740 | 0.4% |
| 48 | 40.822 | 2.20872 | 0.4% |
| 49 | 43.608 | 2.07385 | 0.1% |
| 50 | 47.678 | 1.90588 | 0.3% |
| 51 | 48.210 | 1.88608 | 0.3% |

TABLE 5

| Index | Angle | d Value | Rel. Intensity |
|---|---|---|---|
| 0 | 9.422 | 9.37859 | 31.9% |
| 1 | 10.512 | 8.40852 | 1.4% |

TABLE 5-continued
| Index | Angle | d Value | Rel. Intensity |
|---|---|---|---|
| 2 | 11.118 | 7.95174 | 28.5% |
| 3 | 11.643 | 7.59456 | 84.8% |
| 4 | 12.370 | 7.14996 | 1.6% |
| 5 | 13.199 | 6.70237 | 3.6% |
| 6 | 14.258 | 6.20710 | 35.0% |
| 7 | 15.452 | 5.72986 | 28.9% |
| 8 | 16.995 | 5.21311 | 100.0% |
| 9 | 18.047 | 4.91128 | 2.6% |
| 10 | 19.520 | 4.54396 | 1.2% |
| 11 | 19.910 | 4.45585 | 20.1% |
| 12 | 20.783 | 4.27061 | 38.0% |
| 13 | 21.976 | 4.04131 | 24.2% |
| 14 | 23.388 | 3.80045 | 36.9% |
| 15 | 24.162 | 3.68040 | 4.9% |
| 16 | 24.751 | 3.59417 | 1.5% |
| 17 | 25.228 | 3.52730 | 2.0% |
| 18 | 25.880 | 3.43985 | 1.5% |
| 19 | 26.498 | 3.36103 | 3.9% |
| 20 | 27.301 | 3.26401 | 3.6% |
| 21 | 28.383 | 3.14195 | 3.4% |
| 22 | 28.688 | 3.10931 | 1.7% |
| 23 | 30.059 | 2.97048 | 3.0% |
| 24 | 30.230 | 2.95406 | 3.4% |
| 25 | 30.726 | 2.90756 | 1.3% |
| 26 | 31.123 | 2.87135 | 1.7% |
| 27 | 31.424 | 2.84452 | 6.5% |
| 28 | 32.636 | 2.74160 | 2.2% |
| 29 | 33.432 | 2.67808 | 3.2% |
| 30 | 36.470 | 2.46171 | 1.1% |
| 31 | 36.499 | 2.45980 | 1.2% |
| 32 | 37.251 | 2.41185 | 1.2% |
TABLE 6
| Index | Angle | d Value | Rel. Intensity |
|---|---|---|---|
| 0 | 9.379 | 9.42240 | 0.6% |
| 1 | 10.481 | 8.43369 | 1.7% |
| 2 | 11.078 | 7.98058 | 2.9% |
| 3 | 11.263 | 7.84977 | 0.5% |
| 4 | 11.610 | 7.61575 | 100.0% |
| 5 | 14.188 | 6.23752 | 1.1% |
| 6 | 15.412 | 5.74454 | 0.5% |
| 7 | 16.928 | 5.23343 | 4.4% |
| 8 | 17.279 | 5.12789 | 0.1% |
| 9 | 18.004 | 4.92310 | 0.1% |
| 10 | 18.457 | 4.80323 | 0.4% |
| 11 | 19.870 | 4.46469 | 0.1% |
| 12 | 20.741 | 4.27917 | 0.7% |
| 13 | 21.045 | 4.21805 | 0.4% |
| 14 | 21.931 | 4.04961 | 0.3% |
| 15 | 23.335 | 3.80896 | 19.5% |
| 16 | 23.332 | 3.80945 | 20.8% |
| 17 | 28.324 | 3.14837 | 0.4% |
| 18 | 28.553 | 3.12369 | 0.7% |
| 19 | 28.613 | 3.11721 | 0.5% |
| 20 | 30.050 | 2.97141 | 0.3% |
| 21 | 34.197 | 2.61994 | 0.3% |
| 22 | 34.286 | 2.61330 | 0.2% |
| 23 | 35.300 | 2.54057 | 0.5% |
| 24 | 35.387 | 2.53454 | 0.4% |
Example 8 sets forth a preparation of (S,S)-(+)-crystalline cannabidivarin according the process set forth below:
Preparation of (S,S)-(+)-Cannabidivarin
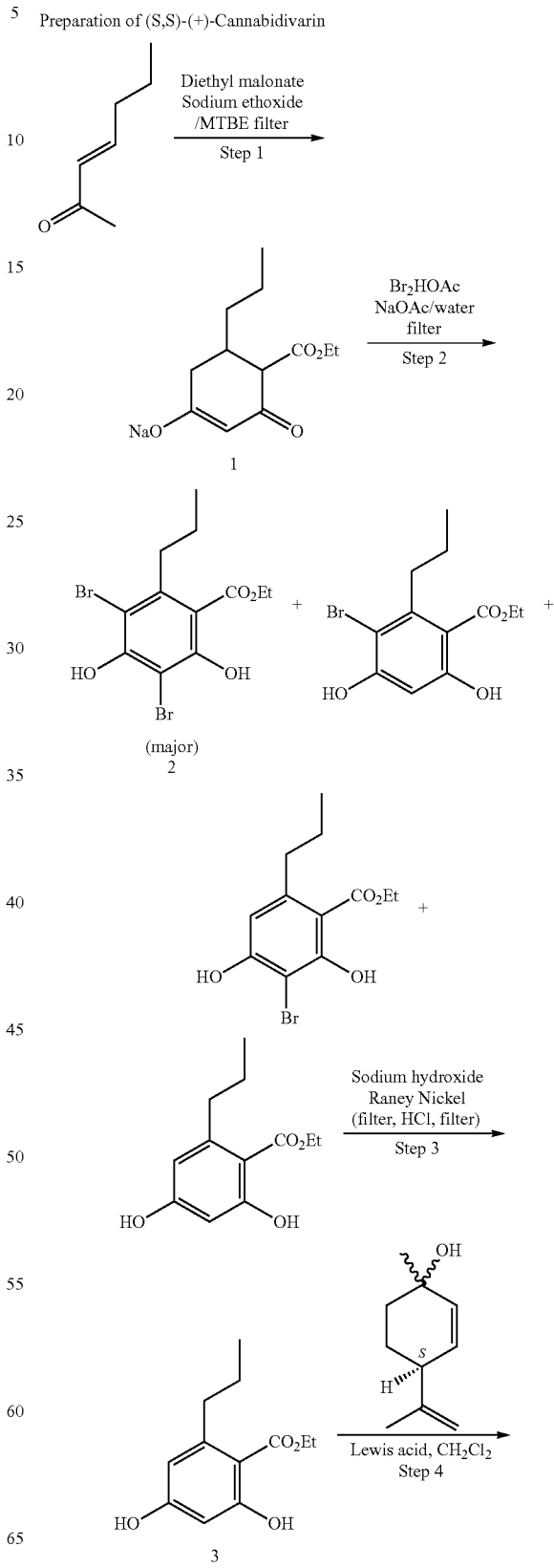

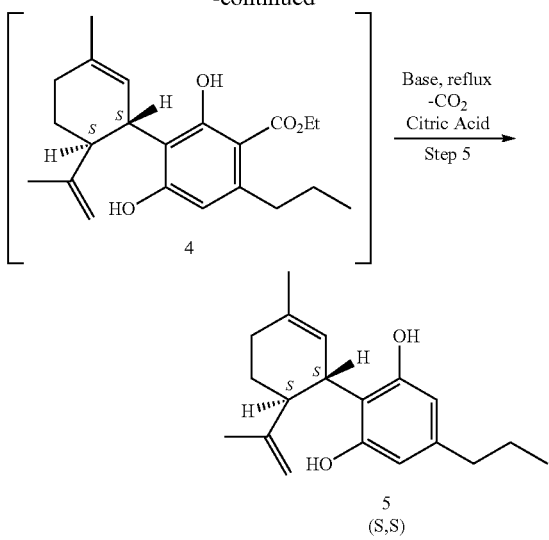

In preparing crystalline cannabidivarin, such as (R,R)-(−)-crystalline cannabidivarin or (S,S)-(+)-crystalline cannabidivarin or substantially pure forms thereof, synthetically-prepared cannabidivarin, is dissolved in a suitable solvent. A suitable solvent is a solvent in which (R,R)-(−)-crystalline cannabidivarin or (S,S)-(+)-crystalline cannabidivarin dissolves such as methyl tert-butyl ether (MTBE). Crystallization may occur by adding an anti-solvent, such as heptane, where crystalline cannabidivarin has more limited solubility. By removing MTBE such as by vacuum, the crystalline cannabidivarin may become concentrated in heptane. Reducing the temperature may then cause crystalline cannabidivarin, such as (R,R)-(−)-crystalline cannabidivarin or (S,S)-(+)-crystalline cannabidivarin as the case may be, to form.

Solid cannabidivarin such as (R,R)-(−)-crystalline cannabidivarin or (S,S)-(+)-crystalline cannabidivarin, which may include substantially pure forms thereof, may be prepared with various different particle size distributions. The particles may be prepared from the synthetic preparations and particle size may be further engineered by micronization or milling. Precipitation rate may also affect particle size. Examples of such distributions (D90) include between about 5 to 200 microns including values and ranges in between such as about 100 to 200 microns, about 50 to 100 microns, about 30 to 50 microns, about 20 to 30 microns, and about 5 to 20 microns. All particle size distributions herein are given as D90 values.

Other embodiments herein provide pharmaceutical compositions or formulations comprising (R,R)-(−)-crystalline cannabidivarin or (S,S)-(+)-crystalline cannabidivarin, which may include substantially pure forms thereof, as described herein and optionally one or more pharmaceutically acceptable excipients. Methods for preparing such formulations or compositions are provided herein.

Compositions or formulations are formulated, dosed, and administered in a fashion consistent with good medical practice. Factors for consideration in this context include the particular medical disorder being treated, the particular patient being treated, the clinical condition of the individual patient, the cause of the disorder, the site of delivery of the agent, the method of administration, the scheduling of administration, and other factors known to medical practitioners.

Solid cannabidivarin, such as (R,R)-(−)-crystalline cannabidivarin or (S,S)-(+)-crystalline cannabidivarin, which may include substantially pure forms thereof, can be formulated to be administered by any suitable means, including oral, topical (including buccal and sublingual), rectal (e.g., suppositories), vaginal, transdermal, parenteral, subcutaneous, intraperitoneal, intrapulmonary, intradermal, intrathecal and epidural and intranasal (such as nasal sprays), and, if desired for local treatment, intralesional administration. Parenteral infusions include intramuscular, intravenous, intraarterial, intraperitoneal, or subcutaneous administration.

Solid cannabidivarin, such as (R,R)-(−)-crystalline cannabidivarin or (S,S)-(+)-crystalline cannabidivarin, which may include substantially pure forms thereof, can be administered in any convenient administrative form (e.g., tablets, gel caps, powders, capsules, solutions, dispersions, suspensions, liposomes, microsomes, syrups, sprays, suppositories, gels, emulsions, patches.) Such compositions can contain components conventional in pharmaceutical preparations (e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants.) They can also contain still other therapeutically active substances. Such formulations may also be delivered in liquid form where the cannabidivarin has been sourced as a solid such as a crystalline solid. Such liquid forms include oral liquid dosage forms including liquid solutions, liquid emulsions, solid-liquid emulsions, for example. The formulations may be prepared so as to be sustained release, extended release, or as a prodrug to promote extended release.

A typical formulation is prepared by mixing a solid or crystalline cannabidivarin, such as (R,R)-(−)-crystalline cannabidivarin or (S,S)-(+)-crystalline cannabidivarin, which may include substantially pure (S,S)-(+)-crystalline cannabidivarin or substantially pure (R,R)-(−)-crystalline cannabidivarin as described herein and a pharmaceutically acceptable excipient. Suitable excipients are well known to those skilled in the art and are described in detail in, e.g., Allen L. V. et al., Ansel's Pharmaceutical Dosage Forms and Drug Delivery Systems (2005) Lippincott, Williams & Wilkins; Allen L. V. et al., Remington: The Science and Practice of Pharmacy (2012) Pharmaceutical Press; and Rowe R. C, Handbook of Pharmaceutical Excipients (2006) Pharmaceutical Press. Once formulated, the solid cannabidivarin may be retained in solid, such as in crystalline form. Alternatively, the solid cannabidivarin may be changed into a non-solid form, such as a liquid form, in the formulation. Accordingly, one embodiment of the invention is a method of making a pharmaceutical formulation, which comprises contacting the solid cannabidivarin with a pharmaceutically acceptable liquid to form the pharmaceutical formulation.

The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives.

The dosages at which solid cannabidivarin, such as (R,R)-(−)-crystalline cannabidivarin or (S,S)-(+)-crystalline cannabidivarin, which may include substantially pure forms thereof, may be administered can vary within wide limits and will, of course, be fitted to the individual requirements in each particular case. In some embodiments, in the case of oral administration, a daily dosage of about 0.01 to 1000 mg per kg of solid cannabidivarin, such as (R,R)-(−)-crystalline cannabidivarin or (S,S)-(+)-crystalline cannabidivarin, which may include substantially pure forms thereof, may be appropriate. In a clinical trial utilizing non-synthetically-prepared cannabidivarin for the treatment of focal seizures, the formulated product, known as GWP42006, was dosed twice per day at 400 mg each (Clinicaltrials.gov Identifier NCT02369741) in the treatment portion of the study. Other dosages include 5 mg/kg/day and 25 mg/kg/day and values in such as about 6, 7, 8, 9, 10, 11, 12, 13, 14, 15, 16, 17, 18, 19, 20, 21, 22, 23, and 24 mg/kg/day.

The term "pharmaceutically effective amount" as used herein, refers to that amount of solid cannabidivarin, such as (R,R)-(−)-crystalline cannabidivarin or (S,S)-(+)-crystalline cannabidivarin, which may include substantially pure forms thereof, that elicits the biological or medicinal response in a tissue system, animal or human that is being sought by a researcher, veterinarian, medical doctor or other clinician, which includes alleviation of the symptoms of the disease or disorder being treated. The specific pharmaceutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with crystalline cannabidivarin; and like factors well known to the researcher, veterinarian, medical doctor or other clinician of ordinary skill. For example, in animal studies, as set forth in U.S. Pat. No. 9,125,859, cannabidivarin prepared by non-synthetic methods was dosed at 50 and 100 mg/kg when delivered intra-peritoneally for the treatment of epilepsy and was effective in reducing mortality at said doses. When delivered for treatment, the formulation may contain solid cannabidivarin, such as (R,R)-(−)-crystalline cannabidivarin or (S,S)-(+)-crystalline cannabidivarin, which may include substantially pure forms thereof. When delivered for treatment, the formulation may contain cannabidivarin in a non-solid form, such as in a liquid state, wherein the cannabidivarin was sourced as a solid form, such as a crystalline form, an example being (S,S)-(+)-crystalline cannabidivarin such as (S,S)-(+)-crystalline cannabidivarin, or (R,R)-(−)-crystalline cannabidivarin or substantially pure (R,R)-(−)-crystalline cannabidivarin.

Having generally described the invention, reference to certain examples, which are provided herein for the purposes of illustration, and are not intended to be limiting unless otherwise specified, may be helpful to illustrate certain embodiments of the invention.

EXAMPLES

Example 1—Instrumentation

Chromatographic separation and purification were performed by a number of methods. Column chromatography and flash chromatography were performed using silica gel (Sorbent Technologies, Catalog number 52500-05). HPLC analyses were performed on a Hewlett Packard series 1100 HPLC instrument. Both Proton and Carbon NMR data were recorded on a Bruker 400 Ultrashield instrument (400 MHz and 100.6 MHz, respectively) BZH 377/400/70F, D 207/54-4146. The NMR spectra were taken in the indicated solvents and chemical shifts are reported in parts per million (ppm) downfield from tetramethyl silane (TMS). Splitting patterns are reported as s, singlet; d, doublet; t, triplet; q, quartet; brs, broad singlet, and m, multiplet as appropriate. Infrared spectra (FTIR) were recorded on an Avatar 360 E.S.P. instrument over 32 scans (DTGS KBr Detector and a KBr Beamsplitter) and are reported in wavenumbers ($cm^{-1}$). Samples were prepared as neat solids. DSC (differential scanning calorimetry) data were obtained on a TA Instruments, DSC Q10. The samples were prepared by transferring 1 mg of the solid compound to a DSC aluminum pan (TA instruments part number 900786.901), covering it with an aluminum lid (TA instruments part number 900779.901) and then crimping the assembly together on a press. This assembly was equilibrated on the instrument at 35° C., 40° C., or 50° C. (Isothermal for 2.00 min) and was heated as indicated herein where the inflection point was experimentally determined and recorded. XRPD results were recorded on a Bruker D2 Phaser (24.6×1.0 mm zero diffraction plate). Melting points were obtained by preparing the samples in a glass capillary tube and running them on a Buchi Melting Point Model B-545 apparatus with a gradient of 0.5° C./min from 114° C. to 124° C. and are uncorrected. Optical rotation was measured on a Rudolph Research Analytical Autopol® V Automatic polarimeter with each reading time averaged over 2 seconds. The microcell size was 1 dm/2 mL with the indicated solvent and concentration (c), reported in grams of solute per 100 mL of solution at the sodium D line (589 nm).

TABLE 7

| Bruker D2 Phaser XRPD Parameters | |
|---|---|
| Instrument Parameter | Value |
| Settings | |
| Radiation Anode | Cu |
| Generator Settings | 30 kV, 10 mA |
| Rotation (Variable Rot) | 15 rpm |
| Scan type | Coupled TwoTheta/Theta |
| Step Time (Time) | 5 seconds |
| Scan Range | Start: 4° and Stop: 40° |
| Step Size (Increment) | 0.01° |
| Air-Scatter Screen | 1 mm |
| LYNXEYE Detector (Solid Angle) | 3°detector opening |
| Primary Optics | |
| Divergence Slit | 0.6 mm |
| Soller Slit Module | 2.5° |
| Secondary Optics | |
| Anti-Scatter Slit | 3 mm |
| Soller Slit Module | 2.5° |
| Filter (Kβ) | Ni 2.5% |

Example 2—Preparation of 2-Hydroxy-4-oxo-6-propyl-cyclohex-1-enecarboxylic Acid Ethyl Ester, Sodium Salt (Compound 1)

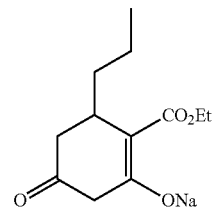

To a 2 L, 4-neck round bottom flask fitted with an overhead stirrer, thermometer, addition funnel, and a reflux condenser was added diethyl malonate (100.0 g, 94.8 mL, 0.624 mol, 1.11 eq) followed by addition of a (65/35) mixture of an ethanol/MTBE solution (respectively), 554 mL. The solution was stirred at room temperature and a solution of 21% sodium ethoxide (221 mL) was added dropwise over 0.75 h where the internal temperature of the reaction mixture increased by 5° C. After the addition was complete, the solution was allowed to stir another 0.25 h and 3-heptene-2-one (63.24 g, 73.5 mL, 0.564 mol, 1.00 eq) was added dropwise over 0.75 h where the internal solution temperature increased another 10° C. The solution was then heated to reflux for 4.5 h, where it was determined to be complete by the disappearance of the enone starting material. It was then allowed to cool to room temperature overnight with stirring. The next day, the solution was cooled to 0° C. with stirring and was then filtered at 0° C. The cake was washed with 150 mL of cold MTBE and was allowed to dry overnight in a vacuum drying oven at 40° C. This provided 108.5 g (77%) of product as a yellow to off-white solid. It was then carried on to the next step without any additional purification. m.p. 252° C. to 259° C. (by DSC). FT-IR (cm$^{-1}$): 2953, 1697, 1582, 1527, 1355, 1273, 1223, 1047, 852, 832, 609 (partial reporting). $^1$H NMR (400 MHz, D$_2$O): 4.22 (q, 2H, J=8 Hz); 3.20 (d, 1H, J=8 Hz); 2.44-2.37 (m, 2H); 2.13-2.06 (m, 1H); 1.48-1.21 (m, 5H); 1.25 (t, 3H, J=8 Hz); 0.85 (t, 3H, J=8 Hz). $^{13}$C NMR (100.6 MHz, DMSO-d6): 190.4, 186.5, 173.0, 99.4, 59.2, 59.1, 40.6, 36.7, 36.2, 18.9, 14.2, 14.1.

Example 3—Preparation of 3,5-Dibromo-2,4-dihydroxy-6-propyl-benzoic Acid Ethyl Ester (Compound 2)

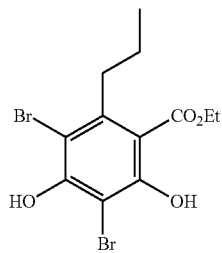 [SMILES: CCCc1c(Br)c(O)c(Br)c(O)c1C(=O)OCC]

To a 3 L, 3-neck flask with a thermometer, overhead stirrer, and an addition funnel was added compound 1 (90.0 g, 0.363 mol, 1.00 eq), sodium acetate (119.0 g, 1.45 mol, 4.0 eq) and acetic acid (504 mL). The solution was warmed to 40° C. with stirring. Bromine (182.8 g, 58.6 mL, 1.14 mol, 3.14 eq) was added dropwise over 2.5 h at a rate where the internal solution temperature was maintained between 40° C.-55° C. As time and temperature increased, the solution became homogeneous. After the addition was completed, the solution was stirred for an additional 1.25 h at 50° C.-55° C. The reaction was deemed complete by HPLC and the solution was then cooled to room temperature. Water, 900 mL, was added dropwise to the stirring solution over 0.75 h and the product began to precipitate from solution after about 450 mL of water were added. After the water addition was complete, the solution was cooled to 15° C.-20° C. and the solids were filtered and washed with water to yield 110.7 g (80%), which was taken into Example 4. An analytically pure sample was prepared by crystallization of the product from heptane. m.p. (by DSC) 77° C.-78° C., lit (*Latvijas PSR Zinatnu Akademijas Vestis, Kimijas Serija* (6) pp. 710-714) 77° C.-78° C. (ethanol/water). FT-IR (cm$^{-1}$): 3466, 2963, 1652, 1553, 1393, 1366, 1308, 1196, 1133, 1020, 1007, 890, 802, 690, 656, 596 (partial reporting). $^1$H NMR (400 MHz, CDCl$_3$): 12.3 (s, 1H); 6.5 (s, 1H); 4.46 (q, 2H, J=8 Hz); 3.85 (t, 2H, J=6 Hz); 1.65-1.55 (m, 2H); 1.45 (t, 3H, J=6 Hz); 1.03 (t, 3H, J=8 Hz)$^{13}$C NMR (100.6 MHz, DMSO-d6): 170.9, 160.0, 154.1, 144.9, 107.8, 105.5, 96.9, 62.7, 37.9, 23.2, 14.4, 14.2.

Example 4—Preparation of 2,4-Dihydroxy-6-propyl-benzoic Acid Ethyl Ester (Compound 3)

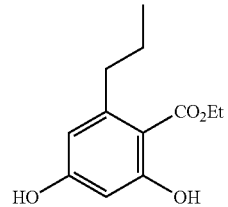 [SMILES: CCCc1cc(O)cc(O)c1C(=O)OCC]

To a 2 L Parr pressure vessel was added compound 2 (95.0 g, 0.249 mol, 1.0 eq) and 1.24 mL of a 1M solution of aqueous sodium hydroxide followed by addition of a Raney Nickel (Type 2800 WR Grace) slurry in water (about 300 g) with stirring. The vessel was sealed and flushed with nitrogen and subsequently was pressurized with hydrogen (5 atm) with rapid stirring as stirring rate affects the reaction rate. The internal solution temperature rose about 5° C. over 3 h and stabilized thereafter. The internal temperature of the vessel was kept below 28° C. over the course of the reaction. After stirring below 28° C. for 24 h, an aliquot was removed and quenched with a trace of citric acid where it was analyzed by HPLC and found to be complete. The solution was then filtered through a celite pad and the residual Raney nickel slurry was washed with 300 mL of water. The aqueous layer was acidified with concentrated HCl (12M) to pH 3 and the aqueous solution was filtered and the precipitate was washed with 100 mL of water to yield a solid, which was dried in a vacuum drying oven overnight at 45° C. to yield 50.7 g of product (91%) as an off-white to faint yellow solid. It was carried onto the next step without any additional purification as traces of water still remain m.p. (96° C.-98° C.), lit (*Latvijas PSR Zinatnu Akademijas Vestis, Kimijas Serija* (6) pp. 710-714) 96° C.-97° C. FT IR (cm$^{-1}$): 3600-3300 broad, 2956, 2862, 1636, 1579, 1403, 1360, 1318, 1263, 1178, 1108, 1014, 841, 717, 620, 574 (partial reporting). $^1$H NMR (400 MHz, CDCl$_3$): 11.76 (s, 1H); 6.28 (d, 1H, J=2 Hz); 6.22 (d, 1H, J=2 Hz); 5.06 (s, 1H); 4.40 (q, 2H, J=8 Hz); 2.84 (t, 2H, J=8 Hz); 1.65-1.55 (m, 2H); 1.42 (t, 3H, J=8 Hz); 0.96 (t, 3H, J=8 Hz). $^{13}$C NMR (100.6 MHz, DMSO-d6): 171.8, 165.6, 160.4, 148.9, 111.1, 105.5, 101.7, 61.6, 39.2, 25.2, 14.4, 14.3.

Example 5—Preparation of (R,R)-(−)-Crystalline Cannabidivarin (Compound 5)

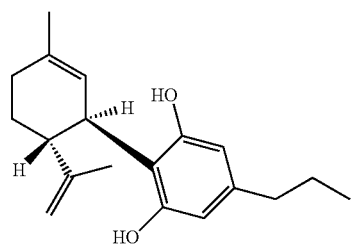 [SMILES: C=C(C)[C@@H]1CCC(C)=C[C@H]1c1c(O)cc(CCC)cc1O]

To a 150 mL round bottom flask with a magnetic stir bar was added compound 3 (3.97 g, 17.7 mmol, 1.00 eq) and sodium sulfate (0.50 g, 3.5 mmol, 0.2 eq) followed by addition of dichloromethane (24 mL). The solution was cooled to −15° C. to −10° C. and 2 separate solutions of borontrifluoride diethyl etherate complex and (+)-4(R)-Para-Mentha-2,8-Diene-1-ol (+PMD) were added simultaneously over 2 h keeping the temperature between −15° C. and −10° C. The amount of PMD was (3.89 g, 4.18 mL, 25.6 mmol, 1.45 eq) and the amount of $BF_3$ etherate was (1.27 g, 1.10 mL, 8.9 mmol, 0.50 eq). There was a slight exotherm upon addition of the boron reagent. The solution was allowed to stir at −15° C. to −10° C. for an additional 4 h. Another (0.38 g, 0.41 mL, 2.5 mmol, 0.14 eq) of PMD was then added and the solution was allowed to warm to room temperature overnight. The next day, the solution was analyzed by HPLC and was found to contain about 10 (a/a) % of 3. The reaction was then quenched with 5% aqueous sodium hydroxide and was allowed to stir at room temperature for 2 h. The stirring was stopped and the layers were separated where only 1.5 (a/a) % of 3 remained in the organic layer. The dichloromethane layer was concentrated and ethanol was added and the solution was concentrated again to remove all the dichloromethane present. The total volume of the crude intermediate in ethanol containing no dichloromethane was approximately 24 mL. A solution of sodium hydroxide (0.64 g) in 11.8 mL of water was added to the ethanol solution containing intermediate 4. Heptane (18 mL) was added and the solution was allowed to stir at room temperature for 1 h and the layers were separated and the heptane layer was discarded. The solution was heated and 12 mL of ethanol was removed and replaced with 12 mL of methanol. A solution of 50% aqueous sodium hydroxide (6 mL) was added, the solution was degassed and was heated to reflux for 4 h, by which time it had proceeded to completion by HPLC. The solution was then cooled to about 10° C.-15° C. and was acidified to pH 5 with approximately 36 mL of 47% aqueous citric acid. The product was extracted with MTBE (30 mL) and the MTBE layer was then washed with 25 mL of saturated aqueous potassium hydrogen carbonate followed by 25 mL of saturated sodium sulfate. The MTBE layer containing product was then filtered through a plug of 3 g silica gel and 1.5 g decolorizing carbon with a celite coated fritted filter funnel. The silica gel plug containing activated carbon and celite was washed with an additional 10 mL of MTBE. To the MTBE solution was added heptane, 30 mL, and the heptane containing solution was concentrated in vacuo to remove all MTBE. The total volume of the solution was eventually 15 mL that contained product plus heptane after all the solvent swap operations were completed. The solution was place in a freezer overnight at −25° C. where the product crystallized. The crystals were filtered the next day and were washed with 2.5 mL of cold, −25° C., heptane. Upon drying 2.12 g of product (7.4 mmol, 42% overall over two steps) that was greater than 99 (a/a) % pure by HPLC. m.p. 116° C.-118° C. (Buchi Melting Point Model B-545). m.p. 117° C.-119° C. (by DSC). $[\alpha]^{25}_D$−117.9 (c 1.00 isopropanol). FT-IR ($cm^{-1}$): 3700-3200 broad, 3050, 2929, 2862, 1627, 1585, 1524, 1439, 1309, 1239, 1148, 1051, 1023, 893, 823, 659, 619, 574 (partial reporting). $^1H$ NMR (400 MHz, $CD_3OD$): 6.15 (s, 2H); 5.36 (s, 1H); 4.54 (s, 1H); 4.50 (s, 1H); 4.05-3.95 (m, 1H); 3.05-2.94 (m, 1H); 2.43 (t, 2H, J=8 Hz); 2.40-2.21 (m, 1H); 2.17-2.08 (m, 1H); 1.90-1.80 (m, 2H); 1.75 (s, 3H); 1.70 (s, 3H) 1.67-1.63 (m, 2H); 0.97 (t, 3H, J=8 Hz). $^{13}C$ NMR (100.6 MHz, $CD_3OD$): 157.6, 150.5, 142.6, 134.5, 127.4, 116.2, 110.6, 108.6, 46.5, 39.0, 37.6, 31.8, 30.9, 25.5, 23.8, 19.7, 14.3. The percent enantiomeric excess of the material was found to be greater than 99% by chiral HPLC analysis employing the method listed in the *Journal of Chromatography A*, 679 (1994) pp. 47-58.

Example 6—Preparing Non-Crystalline Cannabidivarin

All chemicals employed were from Sigma-Aldrich unless otherwise noted. To a nitrogen filled 25 mL round-bottom flask with a thermometer, a nitrogen inlet, and a teflon magnetic stir bar was added 2,4-Dihydroxy-6-propyl-benzoic acid ethyl ester (ethyl varinolate, lot DAD-004-152) (0.25 g, 1.11 mmol, 1.00 eq.); dichloromethane (2.25 mL); magnesium sulfate (75 mg, 0.62 mmol, 0.56 eq), and a solution of (+)-PMD (0.17 g, 1.11 mmol, 1.00 eq) in dichloromethane (1.75 mL). The solution was cooled to 10° C. with the aid of an ice-water bath and solid scandium triflate (Strem, Inc.) (0.84 g, 1.71 mmol, 0.052 eq) was added in one portion. The solution was allowed to stir at 5° C.-15° C. for 5.5 h, by which time the reaction was no longer progressing by HPLC analysis. The reaction was then quenched with the addition of solid sodium carbonate (28 mg, 0.27 mmol, 0.24 eq) at 5° C.-15° C., the cooling bath was removed and the solution was allowed to warm to ambient temperature where it was allowed to stir overnight. The next day, the solids were removed by filtration through a celite pad and the pad was washed with 5 mL of dichloromethane. The resulting solution was concentrated in vacuo to an oil. Heptane (25 mL) was added and the solution was again concentrated to an oil. The resulting oil was dissolved in heptane (50 mL) and it was extracted with 2×15 mL portions of a 20% aqueous sodium hydroxide solution. The heptane layer was dried over sodium sulfate and was concentrated to give 355 mg of a crude oil (89%, unadjusted). 331 mg (0.924 mmol, unadjusted for purity) of this product were taken on directly to the next step without any additional purification.

To a 25 mL round bottom flask was added crude ethyl cannabidivarinolate (331 mg, 0.924 mmol, 1.00 eq), methanol (2 mL), and 50% aqueous sodium hydroxide (2 mL). The solution was allowed to stir at room temperature where it was degassed under vacuum and placed under a nitrogen atmosphere. It was then heated to reflux for 5 h, where it was complete by HPLC analysis. The solution was then allowed to cool to room temperature and it was acidified with 50% aqueous citric acid to pH 5. The product was then extracted with toluene and it was concentrated to a crude oil that was flash filtered through a 1" diameter plug of silica gel (10 g) to yield 0.19 g of product as a light yellow oil at about 96% purity by HPLC, which failed to solidify after several attempts such as solvent exchange to pentane, heptane, and methyl tert-butyl ether. The compound was then placed in a freezer with 1 mL of pure heptane where it remained as an oil after several weeks that separated from the heptane solution at −35° C.

Example 7—Preparing Seed Crystals of Crystalline Cannabidivarin

All chemicals employed were from Sigma-Aldrich unless otherwise noted. To a nitrogen filled 500 mL 3-neck flask with a dropping funnel, thermometer, a nitrogen inlet, and a teflon magnetic stir bar was added 2,4-Dihydroxy-6-propyl-benzoic acid ethyl ester (ethyl varinolate, lot DAD-004-165) (7.35 g, 32.8 mmol, 1.00 eq.); dichloromethane (66 mL); magnesium sulfate (2.21 g, 18.4 mmol, 0.56 eq), and scandium triflate (Strem, Inc.) (0.84 g, 1.71 mmol, 0.052 eq). The solution was cooled to 10° C. with the aid of an ice-water bath. A solution of (+)-PMD (Obiter Labs—Champaign, Ill.) (4.99 g, 5.37 mL, 32.8 mmol, 1.00 eq) dissolved in dichloromethane (21 mL) was added dropwise over 5-10 minutes with rapid stirring keeping the internal temperature of the flask below 15° C. The solution was allowed to stir at 5° C.-15° C. for 5.5 h, by which time the reaction was no longer progressing by HPLC analysis. The reaction was then quenched with the addition of solid sodium carbonate (0.84 g, 7.9 mmol, 0.24 eq) at 5° C.-15° C., the cooling bath was removed and the solution was allowed to warm to ambient temperature where it was allowed to stir for 3 h. The solids were removed by filtration through a celite plug, which was washed with 20 mL of dichloromethane, and the resulting solution was concentrated in vacuo to an oil. Heptane (100 mL) was added and the solution was again concentrated to an oil. The resulting oil was dissolved in heptane (150 mL) and it was extracted with 2×45 mL portions of a 20% aqueous sodium hydroxide solution. The heptane layer was dried over sodium sulfate and was concentrated to give 10.11 g of a crude oil (80%, unadjusted) at approximately 80-90% pure by proton NMR. A portion of this material, 0.94 g, was then subjected to column chromatography by eluting it on a 1" diameter column filled with 50 g of silica gel with a mixture of hexane:toluene (4:1, respectively). The most pure fractions by TLC were combined to provide ethyl cannabidivarinolate (0.54 g) at approximately 99% purity, by HPLC at 224 nm, as an oil. It was then added to a 25 mL round bottom flask and methanol, 3.6 mL, and 50% aqueous sodium hydroxide, 3.6 mL were then added. The stirring solution was degassed under vacuum and placed under a nitrogen atmosphere where it was heated to reflux for 5.5 h, at which time it was shown to be complete by HPLC analysis. The solution was then cooled to room temperature where it was acidified to pH 5 with a 50% aqueous citric acid solution and the product was extracted with toluene (20 mL). The toluene layer was dried over sodium sulfate, 2 g, and was concentrated to an oil. This oil was chromatographed 3 times on a 1" diameter column containing 20 g of silica gel as the solid phase and a toluene:heptane mixture (4:1) as the eluting solvent to yield 0.13 g of cannabidivarin as an oil in greater than 99% purity by HPLC upon concentration. The oil was dissolved in heptane (5 mL) and was concentrated again to 0.13 g. The process was repeated a second time and pentane (2 drops) was added to the oil where it was allowed to stand in a sealed container overnight at −35° C. The next day, crystals were present and a small portion was removed 0.04 g, which was determined to be crystalline by XRPD. m.p. 118° C. This material was identical to the previously prepared lots of cannabidivarin by HPLC and proton NMR.

Example 8—Using Seed Crystals of Example 7 to Crystallize Cannabidivarin

A sample of non-crystalline cannabidivarin of Example 6 was removed from its storage container and was allowed to warm to about 5'C at which temperature the solution became homogeneous. It was seeded with about 1 mg of solid crystalline cannabidivarin from Example 7. The solids propagated in solution and they were removed by filtration to yield 70 mg of crystalline cannabidivarin with a melting point of 120° C. FIG. 8 is an FT-IR spectrum of the material.

Example 9—Preparation of (S,S)-(+)-Crystalline Cannabidivarin

To a 25 mL round bottom flask with a magnetic stir bar was added compound 3 (1.00, 4.46 mmol, 1.00 eq) and sodium sulfate (0.127 g, 0.89 mmol, 0.2 eq) followed by addition of dichloromethane (6.0 mL). The solution was cooled to −15° C. to −10° C. and 2 separate solutions of borontrifluoride diethyl etherate complex and (−)-PMD (Ark Pharm, Inc. Libertyville, Ill.) were added simultaneously over 2.5 hrs keeping the temperature between −15° C. and −10° C. The amount of (−)-PMD was (1.05 g, 1.13 mL, 6.91 mmol, 1.55 eq) and the amount of BF3 etherate was (0.32 g, 0.275 mL, 2.23 mmol, 0.50 eq) diluted with DCM (2.0 mL). There was a slight exotherm upon addition of the boron reagent. The solution was allowed to stir at −15° C. to −10° C. for an additional 5 h. The reaction was then quenched with 5% aqueous sodium hydroxide (6.0 mL) at −5° C. and was allowed to stir and come to room temperature overnight. The stirring was stopped and the layers were separated where only 2.4 (a/a) % of 3 remained in the organic layer. The dichloromethane layer was concentrated and ethanol was added. The solution was concentrated again to remove all the dichloromethane present. The total volume of the crude intermediate in ethanol containing no dichloromethane was approximately 6 mL. A solution of sodium hydroxide (0.19) in 3.42 mL of water was added to the ethanol solution containing intermediate 4. Heptane (5.12 mL) added and the solution was allowed to stir at room temperature for 2.5 hrs and the layers were separated and the heptane layer was discarded. Methanol (4 mL) was added, along with a solution of 50% aqueous sodium hydroxide (0.38 mL). The solution was degassed and was heated to reflux for 24 h, by which time it had proceeded to completion by HPLC. The solution was then cooled to about 10° C.-15° C. and was acidified to pH 5 with approximately 6 mL of 47% aqueous citric acid. The product was extracted with MTBE (10 mL) and the MTBE layer was then washed with 15 mL of saturated aqueous potassium hydrogen carbonate. The MTBE layer containing product was then filtered through a plug of 1.5 g silica gel and 0.75 g decolorizing carbon with a celite coated fritted filter funnel. The silica gel plug containing activated carbon and celite was washed with an additional 10 mL of MTBE. To the MTBE solution was added heptanes (10 mL), and the heptane containing solution was concentrated in vacuo to remove all MTBE and heptane. Column chromatography was performed using 30 g silica gel and 20% toluene in heptanes (1 L). The solvent system was then switched to 40% toluene in heptanes (1 L). Vials containing product of purity ranging between 70% and 80% by HPLC were concentrated under reduced pressure to remove toluene and heptane. After the removal of all solvent, leaving a yellow oil, product crystallized. Heptane (15 mL) was added and the solution was heated to 55° C., dissolving all solids. The solution was cooled to 0° C. and crystals were filtered and washed with 3 mL 0° C. heptanes. Upon drying, 0.3042 g of product (1.06 mmol, 24% overall over two steps) remained. m.p. 118° C.-119° C. (Buchi Melting Point Model B-545). m.p. 119° C. (heptane by DSC). [alpha]25D+116.0° (c 1.00 isopropanol). FT IR (cm−1): 3700-3200 broad, 3050, 2929, 2862, 1627, 1585, 1524, 1439, 1309, 1239, 1148, 1051, 1023, 893, 823, 659, 619, 574 (partial reporting). 1H NMR (400 MHz, CD3OD): 6.16 (s, 2H); 5.36 (s, 1H); 4.54 (s, 1H); 4.50 (s, 1H); 4.05-3.95 (m, 1H); 3.05-2.94 (m, 1H); 2.43 (t, 2H, J=8 Hz); 2.40-2.21 (m, 1H); 2.17-2.08 (m, 1H); 1.90-1.80 (m, 2H); 1.75 (s, 3H); 1.70 (s, 3H) 1.67-1.63 (m, 2H); 0.97 (t, 3H, J=8 Hz). 13C NMR (100.6 MHz, CD3OD): 157.6, 150.5, 142.6, 134.5, 127.4, 116.2, 110.6, 108.5, 46.5, 38.9, 37.6, 31.8, 30.9, 25.5, 23.8, 19.7, 14.6. The percent enantiomeric excess of the material was found to be greater than 99% by chiral HPLC analysis employing the method listed in the *Journal of Chromatography A*, 679 (1994) pp. 47-58.

Example 10—Prophetic Example for Making Amorphous Cannabidivarin

Amorphous cannabidivarin is made by rapid precipitation of a solution made from purified crystalline cannabidivarin and a solvent by adding the solution to an antisolvent with significant agitation. The amorphous cannabidivarin may be (S,S)-(+) cannabidivarin including substantially pure (S,S)-(+) cannabidivarin. It may also be (R,R)-(−)-cannabidivarin such as substantially pure (R,R)-(−) cannabidivarin Example 11—Prophetic Example for Making Amorphous Cannabidivarin A solution made by dissolving purified crystalline cannabidivarin is rapidly spray dried to prepare amorphous cannabidivarin.

The invention claimed is:

1. Crystalline cannabidivarin.
2. (R,R)-(−)-crystalline cannabidivarin or (S,S)-(+)-crystalline cannabidivarin.
3. Crystalline cannabidivarin of claim 1 having a powder x-ray diffraction pattern comprising a peak at about 9.4°2Θ.
4. Crystalline cannabidivarin of claim 1 having a powder x-ray diffraction comprising a peak at about 11.7°2Θ.
5. Crystalline cannabidivarin of claim 1 having a powder x-ray diffraction comprising one or more peaks at about 14.4°2Θ, 15.5°2Θ, or 17.1°2Θ.
6. Crystalline cannabidivarin of claim 1 having a differential scanning calorimetry thermogram comprising a maximum endotherm at between about 116° C. and 120° C.
7. Crystalline cannabidivarin of claim 1 having a melting point of between about 117° C. and 120° C.
8. A pharmaceutical formulation comprising crystalline cannabidivarin of claim 1 and optionally comprising one or more pharmaceutically acceptable excipients.
9. A method of treating epilepsy comprising administering to a patient a pharmaceutically effective amount of crystalline cannabidivarin of claim 1.
10. A method treating cancer comprising administering to a patient a pharmaceutically effective amount of crystalline cannabidivarin of claim 1.
11. A process for making crystalline cannabidivarin of claim 1 comprising synthetically preparing cannabidivarin, adding a solution of the synthetically-prepared cannabidivarin in a suitable solvent to an antisolvent, and removing the suitable solvent to make crystalline cannabidivarin.
12. The process of claim 11, wherein the crystalline cannabidivarin is (R,R)-(−)-crystalline cannabidivarin and the synthetically-prepared cannabidivarin is (R,R)-(−)-cannabidivarin.
13. The process of claim 11, wherein the crystalline cannabidivarin is (S,S)-(+)-crystalline cannabidivarin and the synthetically-prepared cannabidivarin are (S,S)-(+)-cannabidivarin.
14. Crystalline cannabidivarin of claim 1 having an FT-IR spectrum comprising one or more peaks at about 893 $cm^{-1}$, 1585 $cm^{-1}$, 1628 $cm^{-1}$ or 2929 $cm^{-1}$.
15. Crystalline cannabidivarin of claim 2, which is (R,R)-(−)-crystalline cannabidivarin, having substantially the same x-ray powder diffraction pattern of FIG. 3.
16. Crystalline cannabidivarin of claim 2, which is (S,S)-(+)-crystalline cannabidivarin, having substantially the same x-ray powder diffraction pattern of FIG. 16.
17. Crystalline cannabidivarin of claim 2, which is (R,R)-(−)-crystalline cannabidivarin, having substantially the same FT-IR spectrum as FIG. 8.
18. Crystalline cannabidivarin of claim 2, which is (S,S)-(+)-crystalline cannabidivarin, having substantially the same FT-IR spectrum as FIG. 13.
19. A pharmaceutical formulation of claim 8, which comprises (R,R)-(−)-crystalline cannabidivarin or (S,S)-(+)-crystalline cannabidivarin.
20. A method for preparing crystalline cannabidivarin of claim 1, which comprises crystallizing non-crystalline cannabidivarin in the presence of crystalline cannabidivarin seed crystals.
21. Crystalline cannabidivarin of claim 1, which is greater than 99 (a/a) % pure as determined by HPLC.
22. Crystalline cannabidivarin of claim 1, which is synthetically prepared.
23. Crystalline cannabidivarin made by the process of claim 11.

* * * * *